United States Patent
Jalgaonkar et al.

(10) Patent No.: US 11,850,385 B2
(45) Date of Patent: Dec. 26, 2023

(54) BALLOON CATHETER

(71) Applicant: Covidien LP, Mansfield, MA (US)

(72) Inventors: Ujwal Jalgaonkar, Irvine, CA (US); Gaurav Girdhar, Ladera Ranch, CA (US); Eric Mintz, Costa Mesa, CA (US); Alejandra Turcios, Newport Beach, CA (US); Syamala Rani Pulugurtha, Irvine, CA (US)

(73) Assignee: Covidien LP, Mansfield, MA (US)

( * ) Notice: Subject to any disclaimer, the term of this patent is extended or adjusted under 35 U.S.C. 154(b) by 195 days.

(21) Appl. No.: 16/840,109

(22) Filed: Apr. 3, 2020

(65) Prior Publication Data

US 2021/0308431 A1 Oct. 7, 2021

(51) Int. Cl.
*A61M 25/10* (2013.01)
*A61M 25/00* (2006.01)

(52) U.S. Cl.
CPC .... *A61M 25/1002* (2013.01); *A61M 25/0012* (2013.01); *A61M 25/104* (2013.01); *A61M 25/1011* (2013.01); *A61M 25/1018* (2013.01); *A61M 2025/1047* (2013.01)

(58) Field of Classification Search
CPC .......... A61M 25/1002; A61M 25/1011; A61M 25/104; A61M 2025/1086; A61M 2025/1075; A61M 2025/1072; A61M 2025/1061; A61M 2025/1047; A61M 2025/1013; A61M 2025/1015; A61M 25/011
See application file for complete search history.

(56) References Cited

U.S. PATENT DOCUMENTS

| 5,308,356 A | 5/1994 | Blackshear, Jr. et al. |
| 5,383,856 A | 1/1995 | Bersin |
| 5,395,333 A * | 3/1995 | Brill .................. A61M 25/1011 |
| | | 604/101.05 |

(Continued)

FOREIGN PATENT DOCUMENTS

| GB | 2370779 A | 7/2002 |
| WO | 1997004829 A1 | 2/1997 |

(Continued)

OTHER PUBLICATIONS

Peeling et al., "Balloon-assisted guide catheter positioning to overcome extreme cervical carotid tortuosity: technique and case experience," J NeuroIntervent Surg, first published online Mar. 7, 2013, 5 pp.

(Continued)

*Primary Examiner* — Tiffany Legette
(74) *Attorney, Agent, or Firm* — Shumaker & Sieffert, P.A.

(57) ABSTRACT

In some examples, a catheter includes one or more balloons that, when inflated, are configured to be apposition with vasculature or other hollow anatomical structure of a patient to help anchor the catheter within the vasculature, while still permitting fluid to flow past the inflated balloons. When inflated, the one or more balloons define one or more passageways configured to enable fluid to flow past the inflated balloons in a direction along a longitudinal axis of the catheter. For example, the catheter may comprise a plurality of balloons that are circumferentially and longitudinally staggered relative to each other.

18 Claims, 9 Drawing Sheets

(56) References Cited

U.S. PATENT DOCUMENTS

| | | | |
|---|---|---|---|
| 5,545,132 A | 8/1996 | Fagan et al. | |
| 5,855,546 A | 1/1999 | Hastings et al. | |
| 5,947,924 A | 9/1999 | Liprie | |
| 6,478,807 B1* | 11/2002 | Foreman | A61F 2/958 |
| | | | 606/108 |
| 6,508,784 B1 | 1/2003 | Shu | |
| 6,599,230 B2 | 7/2003 | Hastings et al. | |
| 6,730,105 B2 | 5/2004 | Shiber | |
| 6,776,771 B2 | 8/2004 | van Moorlegem et al. | |
| 6,887,267 B2 | 5/2005 | Dworschak et al. | |
| 7,762,985 B2 | 7/2010 | Kabrick et al. | |
| 8,852,207 B2 | 10/2014 | Simpson et al. | |
| 9,011,480 B2 | 4/2015 | Divino et al. | |
| 10,286,184 B2 | 5/2019 | Laduca | |
| 10,327,897 B2 | 6/2019 | Madrid et al. | |
| 2003/0176758 A1* | 9/2003 | Nakano | A61M 25/1027 |
| | | | 600/3 |
| 2008/0021383 A1* | 1/2008 | Pierpont | A61M 25/104 |
| | | | 604/96.01 |
| 2018/0042691 A1* | 2/2018 | Van Helfteren | A61B 18/1492 |
| 2019/0167271 A1* | 6/2019 | Zhadkevich | A61M 25/09 |
| 2019/0167287 A1* | 6/2019 | Vale | A61M 25/1011 |
| 2022/0096257 A1* | 3/2022 | Kallmes | A61F 2/90 |

FOREIGN PATENT DOCUMENTS

| | | |
|---|---|---|
| WO | 9940962 | 8/1999 |
| WO | 1999040971 A1 | 8/1999 |

OTHER PUBLICATIONS

U.S. Appl. No. 15/930,085, filed May 12, 2020, naming inventors Kileen et al.

International Search Report and Written Opinion of International Application No. PCT/US2021/021485, dated Oct. 14, 2021, 17 pp.

* cited by examiner

BALLOON CATHETER

TECHNICAL FIELD

This disclosure relates to a medical catheter.

BACKGROUND

Medical catheters may be used in various medical procedures. For example, a medical catheter may be used to facilitate the delivery of a substance, such as a drug, an embolic substance, or a medical device to a target site within vasculature of a patient. Additionally, or alternatively, a medical catheter may be used to aspirate material (e.g., a thrombus) from a blood vessel or other anatomical structure of a patient.

SUMMARY

In some aspects, this disclosure describes example catheters that include one or more balloons that, when inflated, are configured to be apposition with vasculature (e.g., a blood vessel wall) or other hollow anatomical structure of a patient to help anchor the catheter within the vasculature, while still permitting fluid to flow past the inflated balloons. When inflated, the one or more balloons define one or more passageways (also referred to herein as "fluid passageways") configured to enable fluid, such as blood, to flow past the inflated balloons in a direction along a longitudinal axis of the catheter. For example, the catheter may comprise a plurality of balloons that are circumferentially and longitudinally staggered relative to each other. The separation between the circumferentially and longitudinally staggered balloons may define passageways for fluid to flow from a proximal side of the plurality of balloons to a distal side of the plurality of balloons, or vice versa, in a direction along a longitudinal axis of an elongated body of the catheter, even when the balloons are inflated, extending radially away from the elongated body, and engaged with vasculature.

As another example, the catheter may include a balloon configured to define one or more fluid passageways through which fluid can flow past the inflated balloon in a direction along a longitudinal axis of the catheter when the balloon is inflated. For example, a balloon that extends around an outer perimeter of an elongated body of the catheter may be configured to expand nonuniformly around the outer perimeter, such that the entire perimeter of the balloon (in cross-section) is not in apposition with a blood vessel wall when the balloon is expanded in the blood vessel. The parts of the balloon that are not in apposition with the blood vessel way can define the fluid passageways. In some examples, the balloon is welded to the elongated body in one or more locations to define welded locations at which the balloon is configured to not expand away from the elongated body or expand less than other portions of the balloon. The one or more welded locations may define respective passageways for fluid to flow past the balloon in a direction along a longitudinal axis of the elongated body, even when the balloon is inflated and engaged with vasculature.

The one or more balloons of the catheter defining one or more fluid passageways when inflated may be used to anchor the catheter in vasculature of a patient without occluding blood flow through the vasculature. For example, when inflated, the one or more balloons may engage a blood vessel wall to help hold the catheter in position within the blood vessel, while still enabling blood to flow through the blood vessel past the balloons (either in a distal direction or a proximal direction). In this way, during a medical procedure in which it may be desirable to both hold a catheter in place within the vasculature and not occlude blood flow through a blood vessel in which a catheter is placed, the catheters described herein may reduce or eliminate the need for a clinician to constantly hold the catheter in placed when delivering a medical device, therapeutic agent, aspirating, or taking another action using the catheter.

In some examples, a catheter comprising the one or more balloons defining one or more fluid passageways further comprises a therapeutic neurovascular device within a lumen of the catheter. Anchoring the catheter using the balloon defining the one or more fluid passageways may facilitate a better therapeutic outcome by enabling the catheter to be anchored without blocking blood flow through neurovasculature or through blood vessels used to access the neurovasculature when delivering the therapeutic neurovascular device to the neurovasculature.

Clause 1: In some examples, a catheter comprises: an elongated body defining a lumen; and a plurality of balloons, wherein the balloons of the plurality of balloons are longitudinally and circumferentially staggered along an outer perimeter of the elongated body.

Clause 2: In some examples of the catheter of clause 1, the elongated body defines a longitudinal axis, wherein the balloons of the plurality of balloons are configured to be inflated to an expanded state within a vasculature of a patient to anchor the elongated body within the vasculature, and wherein when the balloons are in an expanded state within the vasculature, the plurality of balloons is configured to permit blood to flow past the plurality of balloons in a direction along the longitudinal axis.

Clause 3: In some examples of the catheter of clause 1 or 2, the balloons of the plurality of balloons are symmetrically arranged about a central longitudinal axis of the elongated body.

Clause 4: In some examples of the catheter of any of clauses 1-3, the plurality of balloons includes: a first set of balloons on a first longitudinal half of the elongated body; and a second set of balloons on a second longitudinal half of the elongated body, the first and second longitudinal halves being on opposite sides of a central longitudinal axis of the elongated body, wherein for each of the first and second sets of balloons, each balloon of the respective set is offset from an adjacent balloon of the respective set in a longitudinal and circumferential direction.

Clause 5: In some examples of the catheter of any of clauses 1-4, each balloon of the plurality of balloons is offset from an adjacent balloon in a longitudinal and circumferential direction.

Clause 6: In some examples of the catheter of any of clauses 1-6, each balloon of the plurality of balloons does not extend around an entire outer perimeter of the elongated body.

Clause 7: In some examples of the catheter of any of clauses 1-6, wherein the balloons of the plurality of balloons are fluidically coupled to the lumen.

Clause 8: In some examples of the catheter of clause 7, the elongated body defines a plurality of lumens including the lumen, at least one of the other lumens of the plurality of lumens being fluidically isolated from the balloons.

Clause 9: In some examples of the catheter of any of clauses 1-6, the elongated body defines a plurality of inflation lumens, and at least two balloons of the plurality of balloons are fluidically coupled to separate inflation lumens of the plurality of inflation lumens.

Clause 10: In some examples, a catheter comprises: an elongated body defining a lumen; one or more balloons along an outer surface of the elongated body, wherein the one or more balloons are configured to enable fluid to flow through vasculature of a patient from a proximal side of the one or more balloons to a distal side of the one or more balloons when the one or more balloons are in an inflated state within the vasculature and engaged with the vasculature; and a therapeutic neurovascular device within the lumen of the catheter.

Clause 11: In some examples of the catheter of clause 10, the balloons of the one or more balloons are symmetrically distributed about a central longitudinal axis of the elongated body.

Clause 12: In some examples of the catheter of clause 10, the balloons of the one or more balloons are asymmetrically distributed about a central longitudinal axis of the elongated body.

Clause 13: In some examples of the catheter of any of clauses 10-12, the one or more balloons comprises a plurality of balloons longitudinally and circumferentially staggered along an outer perimeter of the elongated body.

Clause 14: In some examples of the catheter of any of clauses 10-13, wherein the balloons of the one or more balloons do not extend around an entire outer perimeter of the elongated body.

Clause 15: In some examples of the catheter of any of clauses 10-12 or 14, the one or more balloons is only one balloon welded to the elongated body to define passageways for the fluid to flow through the vasculature from a proximal side of the one balloon to a distal side of the one balloon.

Clause 16: In some examples of the catheter of any of clauses 10-15, the therapeutic neurovascular device comprises a thrombectomy device, an embolic retrieval device, or an implantable medical device. In addition, in any of these examples and the examples described herein, the therapeutic neurovascular device is positioned within an inner catheter that is within the lumen of the elongated body.

Clause 17: In some examples of the catheter of any of clauses 10-16, the implantable medical device comprises a stent, an embolic coil, or a microvascular plug.

Clause 18: In some examples, a method comprises: introducing a catheter into vasculature of a patient, the catheter comprising: an elongated body defining a lumen; and a plurality of balloons, wherein the balloons of the plurality of balloons are longitudinally and circumferentially staggered along an outer surface of the elongated body. The method further comprises anchoring the catheter by inflating the plurality of balloons; and delivering a therapeutic neurovascular device to a target site within the vasculature of the patient via the lumen of the catheter.

Clause 19: In some examples of the method of clause 18, the elongated body defines a longitudinal axis, wherein the balloons of the plurality of balloons are configured to be inflated to an expanded state within the vasculature of the patient to anchor the elongated body within the vasculature, and wherein when the balloons are in an expanded state within the vasculature, the plurality of balloons is configured to permit blood to flow past the plurality of balloons in a direction along the longitudinal axis.

Clause 20: In some examples of the method of clause 18 or clause 19, the balloons of the plurality of balloons are symmetrically arranged about a central longitudinal axis of the elongated body.

Clause 21: In some examples of the method of any of clauses 18-20, the plurality of balloons includes: a first set of balloons on a first longitudinal half of the elongated body; and a second set of balloons on a second longitudinal half of the elongated body, the first and second longitudinal halves being on opposite sides of a central longitudinal axis of the elongated body, wherein for each of the first and second sets of balloons, each balloon of the respective set is offset from an adjacent balloon of the respective set in a longitudinal and circumferential direction.

Clause 22: In some examples of the method of any of clauses 18-21, each balloon of the plurality of balloons is offset from an adjacent balloon in a longitudinal and circumferential direction.

Clause 23: In some examples of the method of any of clauses 18-22, each balloons of the plurality of balloons does not extend around an entire outer perimeter of the outer surface of the elongated body.

Clause 24: In some examples of the method of any of clauses 18-23, the balloons of the plurality of balloons are fluidically coupled to the lumen.

Clause 25: In some examples of the method of any of clauses 18-24, the elongated body defines a plurality of lumens including the lumen, at least one of the other lumens of the plurality of lumens being fluidically isolated from the balloons.

Clause 26: In some examples of the method of any of clauses 18-25, the elongated body defines a plurality of inflation lumens, and at two balloons of the plurality of balloons are fluidically coupled to separate inflation lumens of the plurality of inflation lumens.

Clause 27: In some examples, a method comprises: introducing a catheter into vasculature of a patient, the catheter comprising: an elongated body defining a lumen; and one or more balloons distributed along the elongated body and configured to enable fluid to flow through the vasculature of the patient past the one or more balloons when the one or more balloons are in an inflated state within the vasculature and engaged with the vasculature. The method further comprises anchoring the catheter by inflating the one or more balloons; and delivering a therapeutic neurovascular device to a target site within the vasculature of the patient via the lumen of the catheter.

Clause 28: In some examples of the method of clause 27, the balloons of the one or more balloons are symmetrically distributed about a central longitudinal axis of the elongated body.

Clause 29: In some examples of the method of clause 27, the balloons of the one or more balloons are asymmetrically distributed about a central longitudinal axis of the elongated body.

Clause 30: In some examples of the method of any of clauses 27-29, the one or more balloons comprises a plurality of balloons longitudinally and circumferentially staggered along an outer perimeter of the elongated body.

Clause 31: In some examples of the method of any of clauses 27-30, the balloons of the one or more balloons do not extend around an entire outer perimeter of the outer surface of the elongated body.

Clause 32: In some examples of the method of any of clauses 27-31, the one or more balloons is only one balloon welded to the elongated body to define passageways for the fluid to flow through the vasculature from a proximal side of the one balloon to a distal side of the one balloon.

Clause 33: In some examples of the method of any of clauses 27-32, the therapeutic neurovascular device comprises a thrombectomy device, an embolic retrieval device, or an implantable medical device.

Clause 34: In some examples of the method of any of clauses 27-33, the implantable medical device is a stent, an embolic coil, or a microvascular plug.

The details of one or more aspects of the disclosure are set forth in the accompanying drawings and the description below. Other features, objects, and advantages of the systems and techniques described in this disclosure will be apparent from the description and drawings, and from the claims.

BRIEF DESCRIPTION OF THE DRAWINGS

Like reference characters denoted like elements throughout the description and figures.

DETAILED DESCRIPTION

Figure 1:
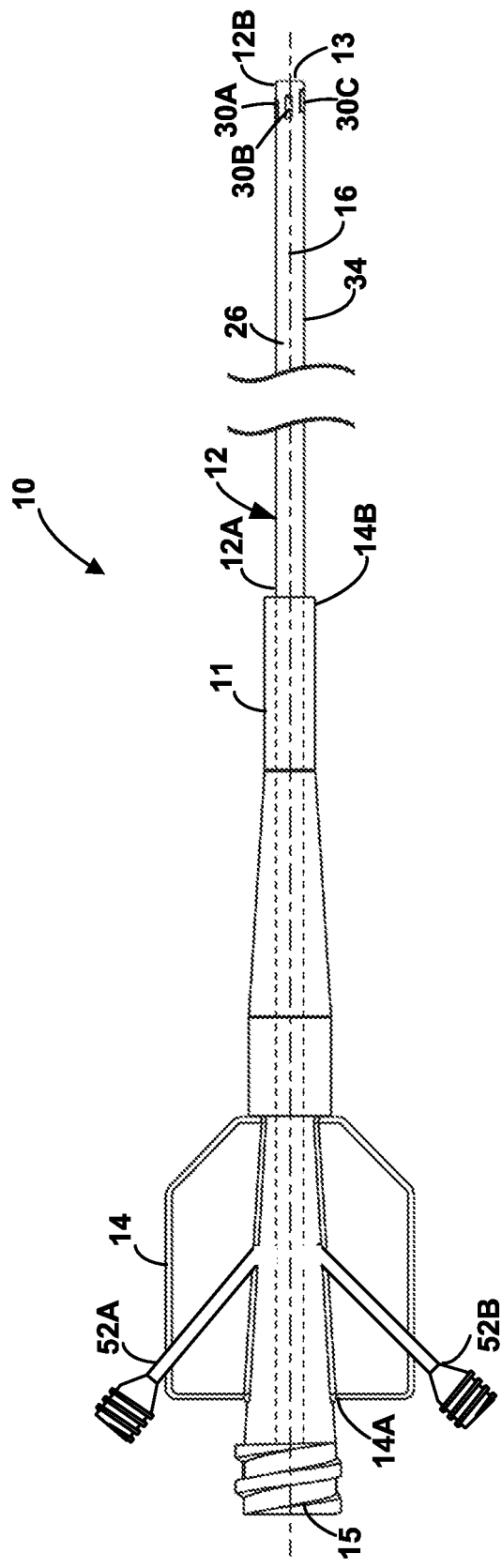
FIG. 1 is a side elevation view of an example catheter, which includes an elongated body, a hub, and one or more expandable balloons.

In examples described herein, a catheter includes one or more balloons that, when inflated, are configured to define one or more fluid passageways through which fluid can flow past the one or more balloons, e.g., when the balloon is in apposition with vasculature (e.g., a blood vessel wall) or other hollow anatomical structure of a patient. Fluid flow past the one or more balloons may refer to fluid flow from a proximal side of the one or more balloons to a distal side of the one or more balloons, or vice versa, in a direction along a longitudinal axis of the catheter. The one or more fluid passageways may be defined by surfaces of the one or more balloons alone or in combination with an outer surface of an elongated body of the catheter from which the one or more balloons radially extend when the balloon is inflated. When a balloon is in apposition with a blood vessel wall (or other hollow anatomical structure), the balloon may engage the vessel wall to help fix the position of the catheter relative to the blood vessel alone or in combination with other balloons of the catheter. Thus, the one or more balloons of example catheters described herein may engage a blood vessel wall (or other hollow anatomical structure) to help anchor the catheter in the blood vessel, while still permitting fluid to flow past the inflated balloons.

While vasculature and blood vessels of a patient are primarily referred to herein, in other examples, the catheters described herein may be within other hollow anatomical structures of a patient.

Example catheters described herein include a relatively flexible elongated body (also referred to as a catheter body or an elongated member in some examples) configured to be navigated through vasculature of a patient, e.g., tortuous vasculature in a brain of the patient. The catheters may each include one or more balloons connected to the elongated body (e.g., an outer surface of the elongated body) and configured to be expanded radially outward away from the elongated body within the vasculature of a patient to contact an inner wall of the vasculature. The one or more balloons may be mechanically connected to the elongated body using any suitable technique, such as, but not limited to, welding, adhering, gluing, heat bonding, laser bonding, attachment mechanisms (e.g., bands on proximal and distal portions of the balloons), or the like or combination of attachment mechanisms. For example, proximal and distal ends of the balloons may be mechanically connected to the elongated body, such that the proximal and distal ends stay connected to the elongated body even when the balloons are inflated.

As discussed above, the one or more balloons of the catheter are configured such that when the balloons are expanded and engaged with a blood vessel wall, fluid may flow past the balloons via the fluid passageways defined by the one or more balloons, rather than occlude blood flow through the blood vessel as in other types of balloon catheters. In some examples, the one or more balloons are a plurality of balloons that are staggered relative to each other along an outer surface of an elongated body of the catheter. For example, in the case of a catheter having a circular cross-sectional shape, the balloons may be circumferentially staggered from each other. In addition or instead, the balloons may be longitudinally staggered from each other. The separation between the staggered balloons results in spaces between the balloons that define passageways for fluid, such as blood, to flow from a proximal side of the plurality of balloons to a distal side of the plurality of balloons, or vice versa, in a direction along a longitudinal axis of the elongated body, even when the balloons are inflated and engaged with vasculature.

In addition to or instead of the plurality of staggered balloons, in some examples, a catheter includes a balloon configured to define one or more passageways for fluid to flow from a proximal side of the balloons to a distal side of the balloons, or vice versa, when the balloon is inflated. Outer surfaces of the (single) balloon define the fluid passageways when the balloon is inflated because the balloon is configured such that when it is inflated in a blood vessel, the entire outer perimeter of the balloon (in cross-section) is not in apposition with the blood vessel wall. For example, the balloon can be configured to be nonuniformly inflated. As an example, the balloon may extend around an outer perimeter of the elongated body and may be welded to the elongated body at one or more locations to form welded locations at which the balloon is configured to not expand away from the elongated body or expand less than other portions of the balloon. The one or more welded locations may define respective passageways for fluid to flow past the balloon in a direction along a longitudinal axis of the elongated body, even when the balloon is inflated and engaged with vasculature.

In some examples of the example catheters described herein, the catheter is configured to deliver a therapeutic neurovascular device to a target treatment site within neurovasculature of a patient. For example, the catheter can be configured to receive the therapeutic neurovascular device within a lumen of the catheter, e.g., directly within the catheter lumen or via a delivery catheter inserted within the catheter lumen. In these examples, the catheter is configured to deliver the therapeutic neurovascular device to a target treatment site within the neurovasculature (also referred to herein as cerebral vasculature in some examples) of a patient. The therapeutic neurovascular device may include any suitable medical device configured to be used to treat a defect in neurovasculature of a patient or used to facilitate treatment of the neurovasculature. For example, the therapeutic neurovascular device can include a thrombectomy device, a flow diverter, a stent, an aspiration catheter, a balloon catheter, a microvascular plug, a filter, an embolic retrieval device (e.g., a stent retriever or an aspiration catheter), or an implantable medical device, such as an embolic coil. As another example, the therapeutic neurovascular device can include a drug delivery catheter.

Example defects in the neurovasculature that the therapeutic neurovascular device can be configured to treat include, but are not limited to, aneurysms, arteriovenous malformations, and vessel occlusions (e.g., caused by a thrombus, atherosclerotic plaque, or foreign bodies). For example, to treat a cerebral aneurysm or an arteriovenous malformation, the therapeutic neurovascular device can include an embolization device, such as embolic coils (which can also be referred to as occlusive coils and/or vaso-occlusive coils), or an embolic substance, or a catheter configured to deliver an embolic substance. As another example, to treat a vessel occlusion, such as thrombosis caused by a thrombus (e.g., a blood clot or other embolus) obstructing neurovasculature of a patient, the therapeutic neurovascular device can include a stent retriever, an aspiration catheter, or other embolic retrieval device. In some medical procedures, a clinician may position an aspiration catheter in a blood vessel of the patient (i.e., catheterization) near the thrombus, apply suction to the aspiration catheter, and engage the thrombus with a tip of the aspiration catheter. This medical procedure may be, for example, A Direct Aspiration First Pass Technique (ADAPT) for acute stroke thrombectomy, or any other aspiration of thrombus or other material from the neurovasculature or other blood vessels.

A clinician may access neurovasculature of a patient via any suitable access point, such as, but not limited to, a femoral artery or a radial artery. In the case of the radial artery access point, a clinician may introduce a catheter into the radial artery via an access point near or on the wrist, hand, or arm of a patient, and navigate the catheter through the radial artery, down through a subclavian artery, into the carotid artery or a vertebral artery, and then into an artery in the brain of the patient. The catheter may be configured to provide a conduit through which other devices may be navigated to the neurovasculature via the carotid artery. Thus, in some cases, a distal portion of the catheter may not extend much more distally into the carotid artery.

The carotid or vertebral artery may be difficult to reach using traditional catheters because the catheter need to make a relatively sharp turn, e.g., a U-turn (e.g., an approximately 180-degree turn) when traversing from a left or right subclavian artery into a left or right common carotid artery, as described in further detail below with reference to FIG. 4. For example, in some cases, such as when the vasculature of a patient is accessed via a radial artery, a catheter may be navigated from a right radial artery to a right subclavian artery, to a right or left carotid artery or a vertebral artery. As another example, the catheter may be navigated from a left radial artery to a left subclavian artery to a right or left carotid artery or a vertebral artery. The present disclosure describes a catheter that is both flexible enough to be navigated from the subclavian artery to the carotid artery (e.g., flexible enough to make the U-turn), and configured to anchor in place within the carotid artery once the catheter is navigated to the carotid artery. In particular, the one or more balloons of the catheter are configured to engage with vessel wall when the one or more balloons are inflated to help hold the catheter in position within the carotid artery and configured to define fluid passageway to allow blood flow past the one or more balloons in a direction along a longitudinal axis of an elongated body of the catheter, even when the balloons are anchored. Thus, the one or more balloons may be referred to as an anchoring mechanism that does not occlude blood flow through the vessel, e.g., from the aorta to the carotid artery. Without the anchoring mechanism described herein, the catheter may tend to slip out of the carotid artery if the clinician is not holding the catheter in place.

In contrast to the anchoring mechanism formed from a relatively rigid wire, the one or more balloons described herein may be relatively compliant, thereby enabling the catheter to be navigated around the relative sharp bend (e.g., 180-degree bend) from a subclavian artery to a carotid artery or a vertebral artery. In contrast, a wired anchoring mechanism may be more rigid and, as a result, more difficult to navigate in general, and to place around the bend.

FIG. 1 is a side elevation view of an example catheter 10, which includes elongated body 12 (also referred to herein as a catheter body in some examples) and hub 14. Hub 14 is positioned at a proximal end of catheter 10 and defines an opening through which an inner lumen 26 (shown in FIG. 2) of elongated body 12 may be accessed and, in some examples, closed. For example, hub 14 may include a Luer connector for connecting to another device, a hemostasis valve, or another mechanism or combination of mechanisms. In some examples, catheter 10 includes strain relief member 11, which may be a part of hub 14 or may be separate from hub 14. In other examples, the proximal end of catheter 10 can include another structure in addition, or instead of, hub 14.

Elongated body 12 extends from proximal end 12A to distal end 12B and defines at least one inner lumen 26 (e.g., one inner lumen, two inner lumens, or three inner lumens) that terminates at distal opening 13 defined by elongated body 12. In some examples, elongated body 12 includes a tubular body. In the example shown in FIG. 1, proximal end 12A of elongated body 12 is received within hub 14 and is mechanically connected to hub 14 via an adhesive, welding, or another suitable technique or combination of techniques. Opening 15 defined by hub 14 and located at proximal end 14A of hub 14 is aligned with inner lumen 26 of elongated body 12, such that inner lumen 26 may be accessed via opening 15.

Hub 14 may include one or more extension members 52A and 52B (collectively "extension members 52") in fluid communication with inflation lumens of elongated body 12. For example, each extension member 52A, 52B may be in fluid communication with a respective inflation lumen or in fluid communication with the same inflation lumen. Extension members 52 can be used to deliver inflation fluid (e.g., saline) to one or more balloons (e.g., balloons 30A-30C shown in FIG. 1 or balloons 30A-30F shown in FIG. 3) distributed around outer surface 34 of elongated body 12 to expand the one or more balloons. Although only extension members 52 are illustrated in FIG. 1, other example catheters may include more than two inflation lumens or less than two inflation lumens.

Elongated body 12 has a suitable length for accessing a target tissue site within the patient from a vascular access point. The length may be measured along a central longitudinal axis 16 of elongated body 12. The target tissue site may depend on the medical procedure for which catheter 10 is used. For example, if catheter 10 is a distal access catheter used to access vasculature in a brain of a patient from a radial artery access point, then elongated body 12 may have a length of about 80 centimeters (cm) to about 120 cm, such as about 85 cm, 90 cm, 95 cm, 100 cm, 105 cm, although other lengths may be used. In other examples, such as examples in which catheter 10 is a distal access catheter used to access vasculature in a brain of a patient from a femoral artery access point, elongated body 12 may have a length of about 100 cm to about 150 cm, such as about 125 cm or 132 cm, although other lengths may be used. Elongated body 12 can have other lengths in other examples.

Elongated body 12 can be relatively thin-walled, such that it defines a relatively large inner diameter for a given outer diameter, which may further contribute to the flexibility and kink-resistance of elongated body 12. For example, in some examples, an outer diameter of elongated body 12 may be about 4 French to about 12 French, such as about 5 French or about 6 French. The measurement term French, abbreviated Fr or F, is three times the diameter of a device as measured in mm. Thus, a 6 French diameter is about 2 millimeters (mm), a 5 French diameter is about 1.67 mm, a 4 French diameter is about 1.33 mm, and a 3 French diameter is about 1 mm. The term "about" as used herein with dimensions may refer to the exact value of the such as when used to describe numerical values, "about" or "approximately" refers to a range within the numerical value resulting from manufacturing tolerances and/or within 1%, 5%, or 10% of the numerical value. For example, a length of about 10 mm refers to a length of 10 mm to the extent permitted by manufacturing tolerances, or a length of 10 mm+/−0.1 mm, +/−0.5 mm, or +/−1 mm in various examples.

In some examples, the diameter of inner lumen 26 (shown in FIG. 2), also referred to herein as an inner diameter of elongated body 12, may be substantially constant along elongated body 12 from proximal end 12A to distal end 12B. For example, an inner diameter of elongated body 12 may have an inner diameter of about 0.07 inches (about 1.78 mm). In other examples, the inner diameter of catheter body 12 may taper from a first inner diameter at a proximal portion that includes proximal end 12A to a second inner diameter at a distal portion that includes distal end 12B, the second inner diameter being smaller than the first inner diameter. For example, an inner diameter of catheter body 12 may taper from a first inner diameter of about 0.0685 inches (about 1.74 mm) to a second inner diameter of about to 0.0605 inches (about 1.54 mm).

In some examples, at least a portion of outer surface 34 of elongated body 12 includes one or more coatings, such as, but not limited to, an anti-thrombogenic coating, which may help reduce the formation of thrombi in vitro, an anti-microbial coating, and/or a lubricating coating. The lubricating coating may be configured to reduce static friction and/kinetic friction between elongated body 12 and tissue of the patient as elongated body 12 is advanced through the vasculature. The lubricating coating can be, for example, a hydrophilic coating. In some examples, the entire working length of elongated body 12 (from distal portion 14B of hub 14 to distal end 12B of elongated body 12) is coated with the hydrophilic coating. In other examples, only a portion of the working length of elongated body 12 coated with the hydrophilic coating. This may provide a length of elongated body 12 distal to hub 14 with which the clinician may grip elongated body 12, e.g., to rotate elongated body 12 or push elongated body 12 through vasculature or other hollow anatomical structure of a patient.

In some examples, elongated body 12 may include one or more radiopaque markers which may help a clinician determine the positioning of catheter 10 relative to a target treatment site. For example, one or more radiopaque markers may be positioned proximal, within elongated body 12, adjacent to balloons 30, or combinations thereof.

As described in further detail below, elongated body 12 may be used to access relatively distal locations in a patient, such as the middle cerebral artery (MCA), the Circle of Willis, and tissue sites more distal than the MCA and the Circle of Willis. The distal locations can be access using, for example, anterior or posterior access. Anterior access can include, for example, navigation through a carotid artery to the MCA/internal carotid artery (ICA) toward the Circle of Willis, and posterior access can include, for example, navigation through a vertebral artery to a basilar artery toward the Circle of Willis. The MCA, as well as other vasculature in the brain or other relatively distal tissue sites (e.g., relative to the vascular access point), may be relatively difficult to reach with a catheter, due at least in part to the tortuous pathway (e.g., comprising relatively sharp twists and/or turns) through the vasculature to reach these tissue sites. In some examples, elongated body 12 is structurally configured to be relatively flexible and pushable, so that it may navigate through the radial artery, through a subclavian artery, into a carotid artery, and into the vasculature in the brain of the patient. In other examples, catheter 10 is configured as a guide catheter and is intended to provide a pathway to the carotid artery, or a point just distal to the carotid artery, from a radial access point, but not as distal as the MCA or the Circle of Willis. In these examples, elongated body 12 may still be relatively flexible and pushable to enable a clinician to navigate elongated body 12 through a subclavian artery and into a carotid artery or a vertebral artery.

Elongated body 12 includes an anchoring mechanism configured to engage with a vessel wall to help hold catheter 10 in position within the blood vessel, e.g., without the aid of a clinician physically holding elongated body 12 in place or with minimal aid from the clinician. For example, in examples in which catheter 10 is navigated to the cerebral vasculature via a radial access point, an anchoring mechanism of elongated body 12 may be configured to engage with the inner wall of the carotid artery (or other blood vessel) once catheter 10 is navigated to the carotid artery via a radial artery in order to help hold a position of elongated body 12 relative to the carotid artery. Without the anchoring mechanism, elongated body 12 may tend to move, e.g., out of the carotid artery, due to the curvature elongated body 12 traverses in order to extend from a subclavian artery to the carotid artery, as described with reference to FIG. 4. While a clinician may hold elongated body 12 to prevent elongated body 12 from moving away from the carotid artery, holding elongated body 12 in this manner may occupy one hand of a clinician during a medical procedure. Thus, the anchoring mechanisms described herein may help free up the hands of the clinicians during a medical procedure by anchoring elongated body 12 within the vasculature via a structure that is part of catheter 10.

In various examples, the anchoring mechanism includes one or more balloons that, when inflated, are configured to be engaged with the vasculature (or other hollow anatomical structure) of a patient to help anchor catheter 10 within the vasculature, while still permitting fluid to flow past the one or more inflated balloons. In the example shown in FIG. 1 the anchoring mechanism comprises a plurality of balloons 30A-30F (collectively "balloons 30"), which are longitudinally and circumferentially staggered along outer surface 34 of a portion of elongated body 12. While "circumferentially" staggered is primarily referred to herein as describing balloons that are separated from each other in a direction about an outer perimeter of elongated body 12 in a direction orthogonal to longitudinal axis 16, in other examples, the portion of elongated body 12 that includes balloons 30 may not be circular in cross-section. Thus, the balloons in any examples described herein may more generally be considered to be staggered around an outer perimeter of elongated body (in a direction orthogonal to longitudinal axis 16).

Only balloons 30A-30C are visible in view shown in FIG. 1. The separation between balloons 30 define passageways between balloons 30 through which for fluid, such as blood, can flow from a proximal side of the plurality of balloons 30 to a distal side of the plurality of balloons 30, or vice versa, in a direction along central longitudinal axis 16 of elongated body 12, even when balloons 30 are inflated, extending radially away from elongated body 12, and engaged with a vasculature or other hollow anatomical structure of a patient.

Figure 2:
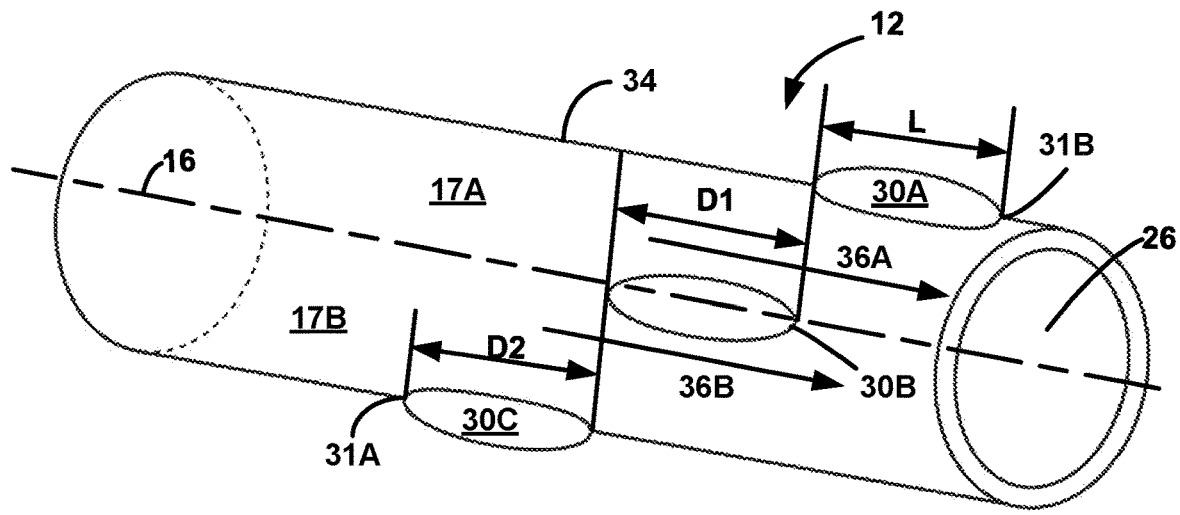
FIG. 2 is an example conceptual side view of a portion of the catheter of FIG. 1 that includes the one or more expandable balloons.
Figure 3:
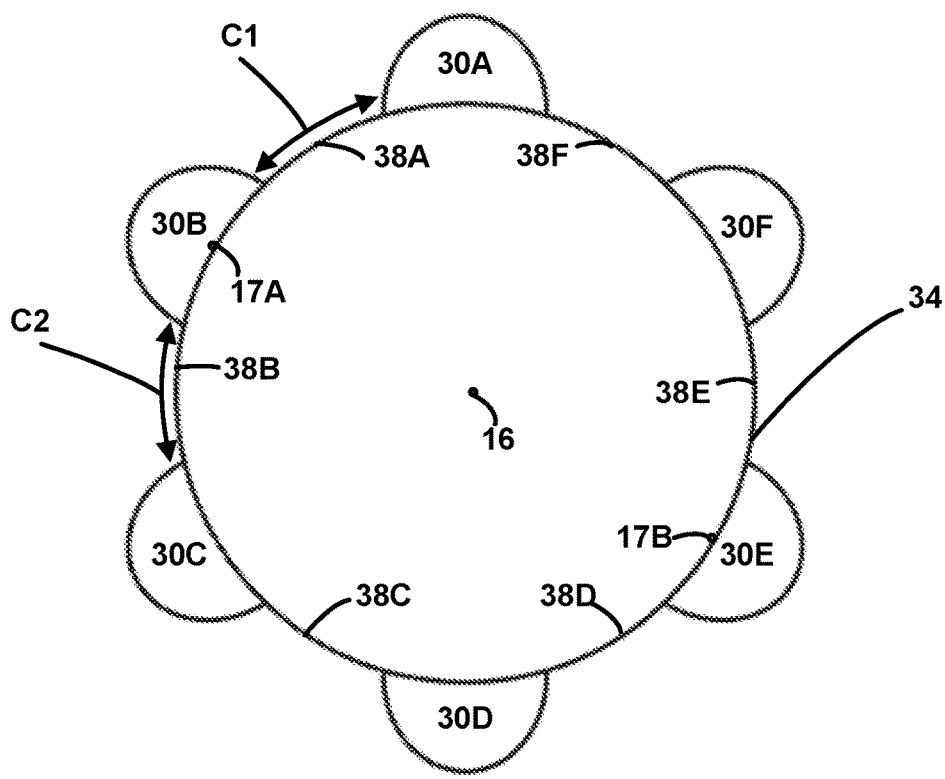
FIG. 3 is an end view of the catheter of FIG. 2, taken along line 33 in FIG. 2.

FIG. 2 is an example conceptual side view of a portion of elongated body 12 of FIG. 1 that includes one or more expandable balloons 30. FIG. 3 is a conceptual end view of the portion of elongated body 12 shown in FIG. 2, and illustrates the balloons 30 in an expanded configuration within carotid artery 47 (shown in FIG. 4). The portion of elongated body 12 shown in FIG. 2 can be a distal portion in some examples, where the distal portion includes distal end 12B of elongated body 12. As another example, the portion shown in FIG. 2 can be a more medial portion or a more proximal portion of elongated body 12.

Balloons 30 can span any suitable length of elongated body 12, where the length is measured along central longitudinal axis 16 of elongated body. In the example shown in FIG. 2 a plurality of balloons 30A-30F are longitudinally and circumferentially staggered along outer surface 34 of a portion of elongated body 12. In some examples, a distance from proximal end 31A of a proximal-most balloon 30 to a distal end 31B of a distal-most balloon 30 is about 2 cm to about 5 cm. Balloons 30 may be positioned any suitable distance from distal end 12B of elongated body 12. In some examples, distal end 31B of a distalmost balloon 30A or 30D is about 0 cm to about 20 cm from distal end 12B of elongated body 12, such as about 0 cm to about 10 cm, or about 10 cm from distal end 12B. In examples in which distal end 31B of a distalmost balloon 30A or 30D is about 0 cm from distal end 12B of elongated body 12, the distal end of the balloon 30A or 30D may be considered to be aligned with distal end 12B of elongated body. In addition, in some examples, proximal end 31A of a proximal-most balloon 30A or 30C is about 5 cm to about 20 cm from distal end 12B of elongated body 12, such as about 5 cm to about 15 cm from distal end 12B.

Balloons 30 are configured to expand from a deflated (e.g., collapsed or uninflated) configuration to an expanded configuration (also referred to herein as an inflated configuration). In some examples, the inflated configuration is a fully expanded configuration, which is the configuration of the balloons 30 at a predetermined maximum inflation pressure, which can be selected to help prevent balloons 30 from bursting. In the deflated configuration, outer surfaces of each balloon 30 are relatively close to outer surface 34 of elongated body 12, and in the expanded configuration, the balloon 30 is expanded radially away from central longitudinal axis 16 such that at least some portions of the outer surfaces of balloons 30 are expanded away from outer surface 34. Thus, in the deflated configuration, a balloon 30 has a relatively low profile configuration, and in the expanded configuration, the balloon 30 has a higher profile configuration compared to the deflated configuration. In some examples, in the expanded configuration, each balloon 30 extends a distance of about 5 mm to 30 mm when fully expanded.

Balloons 30 may be formed from any suitable elastomeric material or a semi-compliant or compliant material, such as, but not limited to, polyethylene, polyethylene terephthalate (PET), nylon, a polyether block amide, polytetrafluoroethylene (PTFE), polyurethane, polyester, silicone, polyvinyl chloride, polypropylene, polyurethanes, polyamides, latex, natural rubber, synthetic rubber, or the like. In some examples, balloons 30 may be made of an expandable material (e.g., made of a stretchable material that expands under pressure) or a wrapped material (e.g., wrapped balloon defining a plurality of pleats that are configured to be wrapped around elongated body 12 while balloons are in a collapsed state and unfurl under pressure.

In some examples, balloons 30 may be formed separate of elongated body 12 and attached to an exterior surface of elongated body 12 via co-extrusion, bonding, adhesives, or the like. In other examples, balloons 30 may be integrally formed with elongated body 12 such that balloons 30 is embedded or at least partially embedded in elongated body 12.

As discussed with reference to FIGS. 5 and 6, balloons 30 are each in fluid communication with an inflation lumen defined by elongated body 12 and are configured to receive an inflation fluid 50 (shown in FIGS. 5 and 6) via the inflation lumen to expand from the deflated configuration to the expanded configuration. Balloons 30 may each be deflated via the inflation lumen as well. In some examples, as discussed with reference to FIG. 5, balloons 30 may each be fluidically coupled to a separate inflation lumen. Instead of or in addition to this configuration, as discussed with reference to FIG. 6, in some examples, at least two balloons 30 may share an inflation lumen.

Balloons 30 may be mechanically connected to elongated body 12 using any suitable technique. In some examples, some of the balloons 30 are attached to outer surface 34 of elongated body 12. For example, the proximal and the distal ends of some of the balloons 30 may be bonded (e.g., via adhesive), crimped, swaged, welded, or otherwise secured to elongated body 12.

In some examples, outer surface 34 of elongated body 12 defines recesses in which one or more of the balloons 30 may be positioned to define a relatively low profile elongated body 12. In these examples, the one or more balloons 30 may still be considered to be attached to outer surface 34 of elongated body 12. The recesses may have any suitable depth. In some examples, a balloon is completely contained within the recess in its deflated configuration, i.e., no part of the balloon protrudes past the outermost part of outer surface 34 of elongated body 12. In other examples, a balloon is only partially contained within the recess when in the deflated configuration, i.e., part of the balloon does not protrude out of the recess, and past outer surface 34 of elongated body 12 and part of the balloon protrudes past outer surface 34.

In some examples, each balloon of balloons 30 extends around less than the entire outer perimeter 34 of elongated body 12 and is spaced from an adjacent balloon to define a passageway between the balloons. For example, balloon 30A is spaced from an adjacent balloon 30B, thereby defining a fluid passageway 36A between the balloons 30A, 30B. In the example shown in FIG. 2, the plurality of balloons 30 includes balloons 30A-30F that are longitudinally and circumferentially distributed relative to each other to define fluid passageways 36A-36F (collectively, "fluid passageways 36") between adjacent balloons when the balloons 30 are inflated. Only fluid passageways 36A-36B are visible in view shown in FIG. 2. For example, balloons 30A-30F are circumferentially spaced from each other about outer perimeter 34 of elongated body 12, balloons 30A-30C are longitudinally spaced from each other along central longitudinal axis 16, and balloons 30D-30F are longitudinally spaced from each other along central longitudinal axis 16. Thus, balloons 30A-30C are longitudinally and circumferentially offset from each other, such that balloons 30A-30C are neither longitudinally nor circumferentially aligned with each other. Balloons 30D-30F are on the opposite side of central longitudinal axis 16 from balloons 30A-30C and are similarly longitudinally and circumferentially offset from each other such that the balloons 30D-30F are neither longitudinally nor circumferentially aligned with each other.

Although six balloons 30 are shown in FIGS. 2 and 3, in other examples, catheter 10 can include any suitable number of balloons such as one balloon (as described with reference to FIG. 8), two, three, four, five, or more than six balloons.

Balloons 30 may have any suitable spacing relative to each other. The spacing can include, for example, a longitudinal spacing along central longitudinal axis 16 or a circumferential spacing in a direction along the outer perimeter of elongated body 12, where the outer perimeter is a perimeter of a cross-section of elongated body 12 in an orthogonal to the central longitudinal axis 16. The circumferential spacing can also be referred to as a tangential spacing in the case of an elongated body 12 having a non-circular cross-section. In some examples, some or all of the balloons 30 are evenly spaced about the outer perimeter of elongated body 12. In the example shown in FIG. 3, the circumferential distance C1 between expandable balloons 30A and 30B may be the same distance as the circumferential distance C2 between expandable balloons 30B and 30C (e.g., separated by a distance of 0.3 mm to about 1 mm). The circumferential distances C1 and C2 are measured along outer surface 34 in a direction orthogonal to longitudinal axis 16. In other examples, some or all of the balloons 30 are unevenly spaced about outer perimeter 34 of elongated body 12. For example, the circumferential distance C1 between expandable balloons 30B and 30A may be greater than the circumferential distance C2 between expandable balloons 30B and 30C. The circumferential distances or other distance measurements between balloons along the outer perimeter of elongated body 12 can be measured, for example, from one side of a balloon to another side, e.g., the closest parts of the adjacent balloons.

In some examples, some or all of the balloons 30 are evenly spaced along central longitudinal axis 16 of elongated body 12. In the example shown in FIG. 2, the longitudinal distance between expandable balloons 30A and 30B (e.g., the distance D1 from the proximal end of expandable balloon 30A to the proximal end of expandable balloon 30B measured in a direction parallel to central longitudinal axis 16) may be the same distance (e.g., separated by a distance of 0 mm to about 30 mm) as the longitudinal distance between expandable balloons 30B and 30C (e.g., the distance D2 from the proximal end of expandable balloon 30B to the proximal end of expandable balloon 30C measured in a direction parallel to central longitudinal axis 16). In other examples, some or all balloons 30 are unevenly spaced along central longitudinal axis 16 of elongated body 12. For example, the longitudinal distance between expandable balloons 30B and 30A may be a greater distance than the longitudinal distance between expandable balloons 30B and 30C (e.g., separated by a distance of about 0 mm to about 50 mm).

Each balloon of expandable balloons 30 may define any suitable length L, which can be measured from proximal end to distal end of the respective balloon. In some examples, the length L of the balloons which may depend, for example, on the size of elongated body 12 and the intended use of catheter 10. For example, each balloon of expandable balloons 30 may have a length L of 2 mm to about 20 mm (e.g., the distance from the proximal end of balloon 30A to the distal end of balloon 30A) to anchor catheter 10 in the carotid artery of the patient.

Balloons 30 can have any suitable orientation relative to central longitudinal axis 16. In some examples, some or all of balloons 30 are oriented relative to central longitudinal axis 16 such that the proximal and distal ends of a respective balloon 30 are aligned along an axis parallel to central longitudinal axis 16. In other examples, some or all of the balloons 30 are skewed relative to central longitudinal axis 16 such that the proximal and distal ends of a respective balloon 30 are not aligned along an axis parallel to central longitudinal axis 16.

The separation between balloons 30A-30F define passageways 36A-36F (collectively "passageways 36") for fluid, such as blood, to flow from a proximal side of balloon 30A to a distal side of balloon 30F, or vice versa, in a direction along central longitudinal axis 16 of elongated body 12, even when balloons 30A-30F are inflated, extending radially away from elongated body 12, and engaged with vasculature. Only fluid passageways 36A-36B are visible in view shown in FIG. 2. Passageways 36A-36F provide spaces for fluid, such as blood, to flow to the brain or other area of the body of a patient, even when the balloons are inflated and anchored in a blood vessel of the patient that leads to the brain or the other area of the body. Two adjacent balloons of expandable balloons 30 defines a respective fluid passageway 36. As shown in FIG. 2, balloons 30A and 30B define fluid passageway 36A, balloons 30B and 30C define fluid passageway 36B, and the like. The total number of and size of the passageways may be defined based on the number of balloons in an expanded state.

In some examples, as shown in FIGS. 2 and 3, balloons 30 are symmetrically distributed about central longitudinal axis 16 of elongated body 12. Elongated body 12 may define two longitudinal halves 17A, 17B, which are divided by central longitudinal axis 16. That is, longitudinal halves 17A and 17B may be on opposite side of central longitudinal axis 16. As shown in FIG. 2, expandable balloons 30 include a first set of balloons 30A-30C on a first longitudinal half 17A of elongated body 12 and a second set of balloons 30D-30F on a second longitudinal half 17B of elongated body 12, and there is a plane of symmetry bisecting central longitudinal axis 16.

In some examples, balloons 30 are asymmetrically distributed about central longitudinal axis 16 of elongated body 12. For example, balloons 30 may include only a set of balloons 30A-30C evenly spaced about longitudinal half 17A of elongated body 12, or balloons 30A-30C on longitudinal half 17A may have a different circumferential and/or longitudinal distribution than balloons 30D-30F on second longitudinal half 17B.

Each balloon of the first set of balloons 30A-30C on first longitudinal half 17A may be offset from a directly adjacent balloon of the first set balloons in longitudinal and circumferential directions (in examples in which elongated body 12 has a circular shape in cross-section, the cross-section taken orthogonal to longitudinal axis 16). For example, directly adjacent balloons 30A and 30B are longitudinally and circumferentially offset from each other and directly adjacent balloons 30B, 30C are longitudinally and circumferentially offset from each other, e.g., by the example distances described above. Similarly, each balloon of the second set of balloons 30D-30F on second longitudinal half 17B may be offset from an adjacent balloon of the second set balloons in longitudinal and circumferential directions. For example, directly adjacent balloons 30D, 30E are longitudinally and circumferentially offset from each other and directly adjacent balloons 30E, 30F are longitudinally and circumferentially offset from each other.

In examples in which balloons 30 are symmetrically arranged relative to central longitudinal axis 16, some balloons 30 on first longitudinal half 17A may be longitudinally aligned with another balloon 30 on second longitudinal half 17B. For example, balloon 30A may be longitudinally aligned with balloon 30F, balloons 30B may be longitudinally aligned with balloon 30E, and balloon 30C may be longitudinally aligned with balloon 30D.

In some examples in which balloons 30 are asymmetrically arranged relative to central longitudinal axis 16, some or all of the balloons 30A-30F are offset from a directly adjacent balloon of the first set balloons in longitudinal and circumferential directions. For example, directly adjacent balloons 30A and 30B are longitudinally and circumferentially offset from each other, directly adjacent balloons 30B, 30C are longitudinally and circumferentially offset from each other, directly adjacent balloons 30C, 30D are longitudinally and circumferentially offset from each other, directly adjacent balloons 30D, 30E are longitudinally and circumferentially offset from each other, directly adjacent balloons 30E, 30F are longitudinally and circumferentially offset from each other, and directly adjacent balloons 30A, 30F are longitudinally and circumferentially offset from each other. As another example, balloons 30A, 30F may be circumferentially offset, but longitudinally aligned whereas balloons 30B, 30E can be circumferentially and longitudinally offset. Several different combinations of alignments between balloons 30 are possible.

Although the circumferential direction is primarily referred to herein for ease of description, in other examples, elongated body 12 defines a non-circular shape in cross-section, and the circumferential direction referred to in the examples described herein may instead be a direction along the outer perimeter of the non-circular shape.

While a plurality of physically separate balloons 30 are shown in FIGS. 1-3, in some examples, at least two expandable balloons 30 shown in these figures may be lobes defined by a single balloon. The lobes can be defined by, for example, a respective expandable section of the balloon. The lobes can be defined using any suitable technique, such as by adhering or welding the single balloon to outer surface 34 of elongated body 12 at locations 38A-38F. Thus, locations 38A-38F may correspond to respective passageways 36 for fluid to flow past balloon 30 in a direction along central longitudinal axis 16 of elongated body 12, even when the balloon 30 is inflated and engaged with vasculature.

Thus, in some examples, rather than include a plurality of separate balloons 30, catheter 10 includes a single balloon configured to be nonuniformly inflated to define balloon lobes 30 that look like the separate balloons 30 shown in FIGS. 1-3, as well as other figures described herein. The outer perimeter of the single balloon can define the fluid passageways 36 when the single balloon 30 is inflated because the single balloon is configured such that when it is inflated, only portion of the balloon is engaged with a blood vessel wall. The balloon may extend around the outer perimeter of elongated body 12 and may be welded in locations 38A-38F to define fluid passageways 36 when the balloon is in an expanded state.

In contrast to a single balloon, a catheter including a plurality of separate balloons 30 may enable a clinician to inflate a subset of balloons 30 (e.g., one balloon or more than one balloon but less than all the balloons 30) selectively during a medical procedure. This may enable a clinician to tailor the anchoring mechanism to a target anchor site by selecting the balloons 30 to expand based on a length of the blood vessel in which elongated body 12 will be anchored. In addition, configurating catheter 10 to enable selective inflation of balloons 30 may enable the clinician to selectively leave one or more balloons 30 deflated to avoid blocking branching vessels (e.g. if one of the balloons is positioned in front of the external carotid artery (ECA)). An ability to selective inflate a subset of balloons 30 may also enable a clinician to use the balloons 30 to, for example, facilitate navigation of elongated body 12 to a target site within a patient. For example, a clinician may selectively inflate balloon 30B to its expanded state while leaving balloons 30A and 30C-30F fully deflated or only partially inflated in order to better center elongated body 12 in a blood vessel, e.g., when navigating elongated body 12 around a curve. Better centering elongated body 12 in a blood vessel may help prevent or reduce the occurrence of a catheter ledge-effect, thereby improving the ease with which a clinician may guide the catheter to a relatively distal vasculature treatment site through a series of tight turns in the vasculature. A ledge-effect may otherwise cause distal end 12B of elongated body 12 to catch on or abrade certain anatomical features as it is advanced through vasculature of the patient, which may adversely affect the navigability of the catheter.

Figure 4:
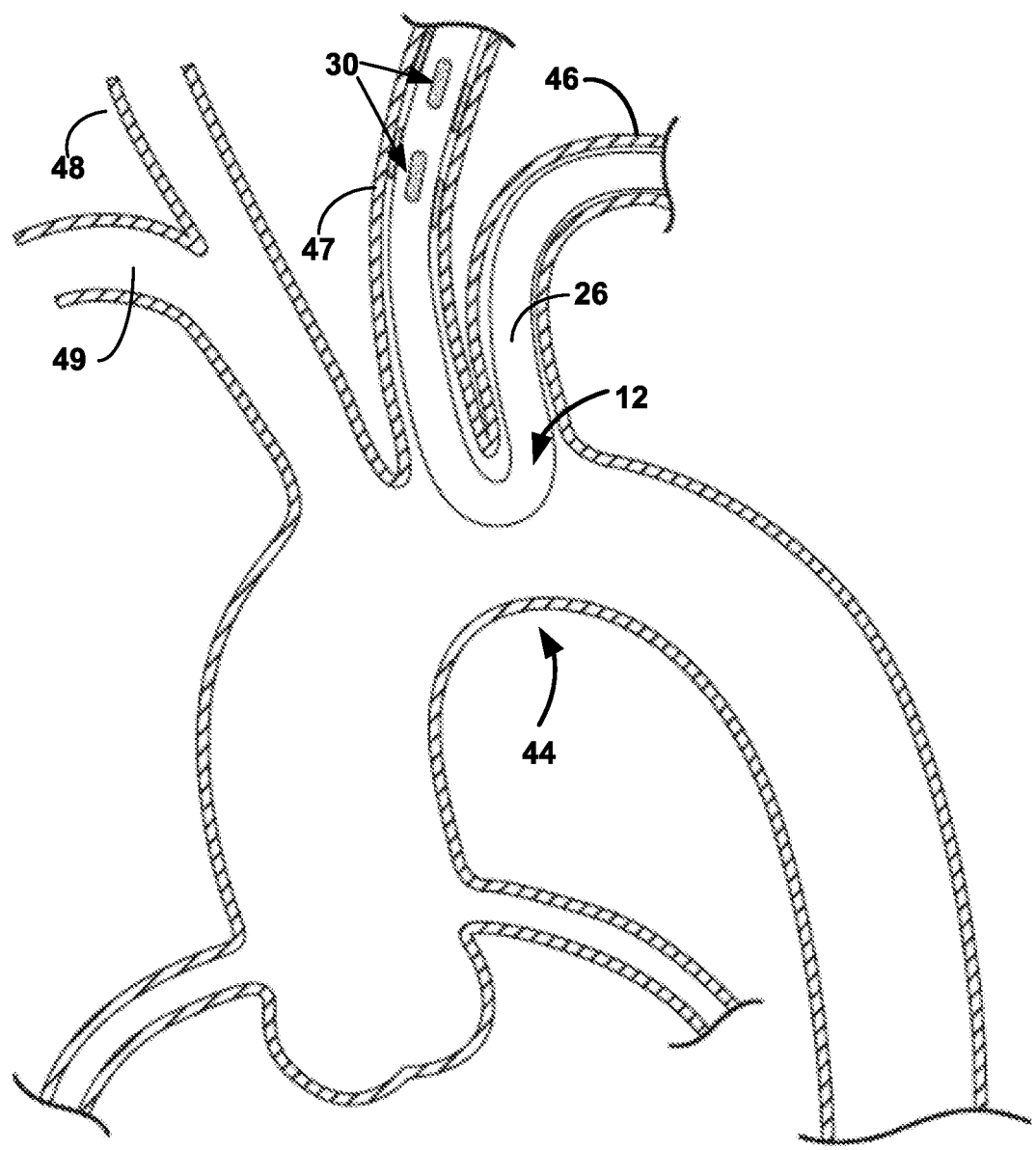
FIG. 4 is a schematic illustration of the catheter of FIG. 2 in a carotid artery of a patient.

FIG. 4 is a conceptual illustration of elongated body 12 of catheter 10 introduced in a subclavian artery 46 and a carotid artery 47 of a patient. For example, elongated body 12 may extend from a radial artery access point to subclavian artery 46 and into carotid artery 47. Although catheter 10 is shown in a left subclavian artery 46 and a left common carotid artery 47 in FIG. 4, in other examples, catheter 10 can be navigated into a right common carotid artery 48 from the left subclavian artery 46 or into left common carotid artery 47 from a right subclavian artery 49, e.g., from a radial artery access point. In some examples, a clinician may guide distal end 12B of elongated body 12 to a location in the carotid artery 47, as shown in FIG. 4. For example, catheter 10 may function as a guide catheter, and another catheter may be inserted inside lumen 26 of elongated body 12 of catheter 10 and extend distally past distal end 12B of elongated body 12 to reach a target site in the brain of the patient. In other examples, distal end 12B of elongated body 12 may be guided to a target site within the brain of a patient.

In some medical procedures, a clinician may advance elongated body 12 from a radial access point and through a left or right subclavian artery 46, 49 to a left or right carotid artery 47, 48. In some examples, the clinician may navigate elongated body 12 to carotid artery 47, 48 with the aid of a guide member, such as, but not limited to, a guidewire or an inner catheter. As shown, to traverse from a subclavian artery 46 or 49 to a carotid artery 47 or 48, elongated body 12 takes a relatively sharp turn (e.g., a U-turn). In some cases, elongated body 12 may tend to want to move back into aortic arch 44 from carotid artery 47 due to the anatomy and, in some cases, the stiffness of elongated body 12. When catheter 10 does not include an anchoring mechanism, a clinician may hold onto a portion of elongated body 12 that is outside the body of the patient in an attempt to keep elongated body 12 within carotid artery 47. While this may be effective, it may also be desirable to free the clinician's hand for other tasks. Plurality of balloons 30 of catheter 10 (or a single balloon in other examples) is configured to help anchor elongated body within carotid artery 47, thereby enabling the clinician to keep both hands free.

After elongated body 12 is navigated from subclavian artery 46 to carotid artery 47, the clinician may expand balloons 30 from the deflated state (also referred to herein as a collapsed state) to the inflated state (also referred to herein as an expanded state) to anchor elongated body 12 in carotid artery 47, as shown in FIG. 4. Balloons 30 may engage the interior wall of carotid artery 47 to help anchor catheter 10 in carotid artery 47, while still permitting fluid to flow through fluid passageways 36 (e.g., as shown in FIG. 2) and past the inflated balloons 30. Thus, balloons 30 are configured to anchor elongated body 12 within carotid artery 47 without blocking blood flow from aortic arch 44 to carotid artery 47, which may enable a clinician to keep catheter 10 in carotid artery 47 of the patient for a longer period of time.

Figure 5:
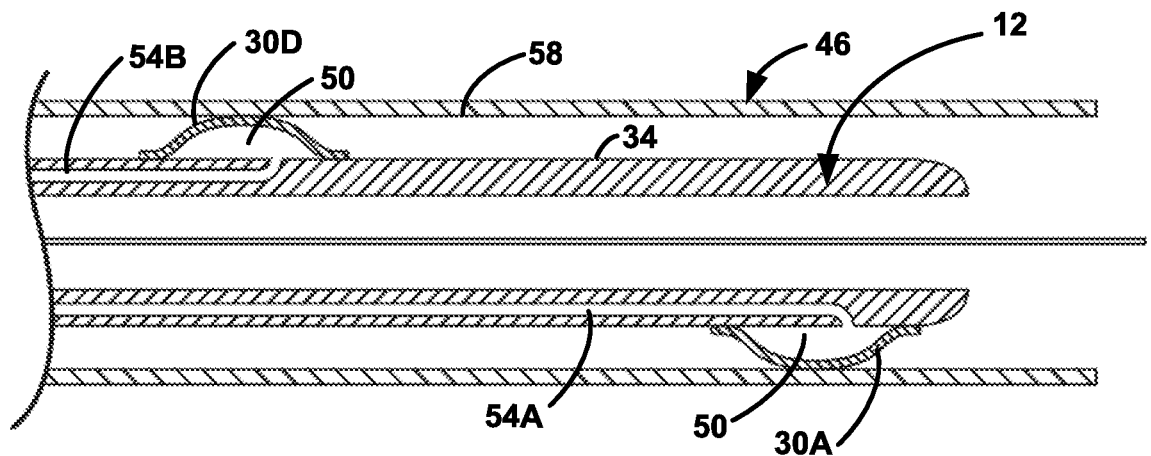
FIG. 5 is a schematic cross-sectional view of the catheter of FIG. 2 in a carotid artery and illustrates the plurality of balloons in an expanded state, where the cross-section is taken along a central longitudinal axis of the elongated body.
Figure 6:
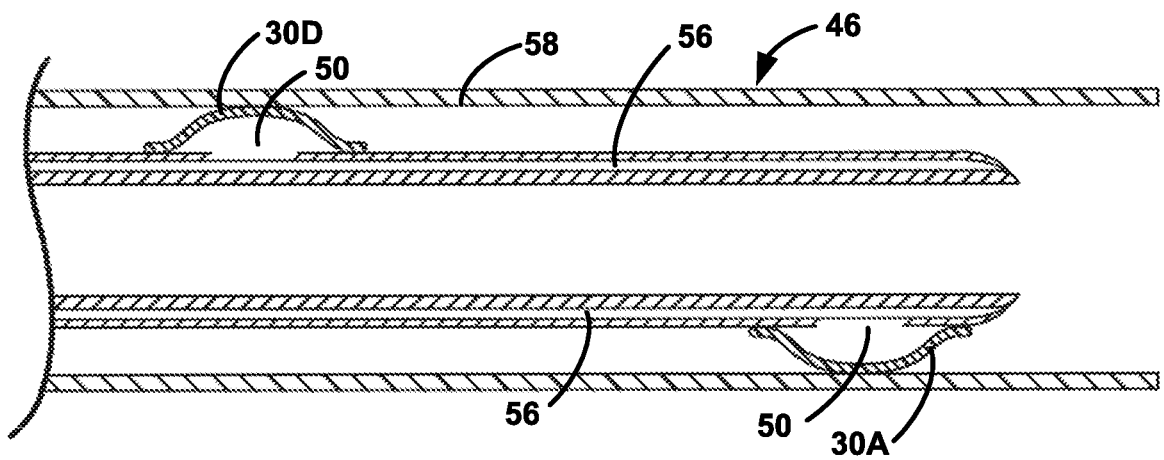
FIG. 6 is a schematic cross-sectional view of another example of the catheter of FIG. 2 in a carotid artery and illustrates the plurality of balloons in an expanded state, where the cross-section is taken along a central longitudinal axis of the elongated body.

FIG. 5 is a conceptual cross-sectional view of elongated body 12 in carotid artery 47 (or other target vascular location), with balloons 30 in an expanded configuration, the cross-section being taken in a direction parallel to central longitudinal axis 16 of elongated body 2. Although only balloons 30A and 30D are shown in the particular cross-sectional view shown FIG. 5, in other examples, elongated body 12 can include any suitable number of balloons in the cross-sectional view shown in FIG. 5, and the number of balloons shown in the particular view of FIG. 5 depends on the arrangement of the balloons 30 along the outer surface 34 of elongated body 12.

After elongated body 12 is navigated to a target site within carotid artery 47 (or such other target vascular location), balloons 30 may be inflated with inflation fluid 50 (e.g., saline, phosphate buffered saline (PBS), a contrast agent, such as iodine, or another suitable biocompatible material) to an expanded state in which balloons 30 engage with inner wall 58 of carotid artery 47, as shown in FIG. 5. For example, inflation fluid 50 can include a combination of a contrast agent and saline in any suitable ratio, such as, but not limited to, 50/50, 70/30, and 40/60.

As discussed above, in some examples, some or all of the balloons 30 may be inflated via inflation fluid 50 delivered by multiple inflation lumens. As shown in FIG. 5, elongated body 12 defines at least two separate inflation lumens 54A and 54B, which may be fluidically coupled to respective balloons 30A and 30D and to respective extension members 52A, 52B (FIG. 1). Thus, for example, inflation lumen 54B is fluidically isolated from and not fluidically coupled to balloon 30A, and inflation lumen 54A is fluidically isolated from and not fluidically coupled to balloon 30D.

In examples in which multiple balloons 30 are fluidically coupled to respective inflation lumens, e.g., as shown in FIG. 5, the multiple balloons 30 may be separately inflated. This may enable a clinician to separately inflate balloons 30 to aid navigation of elongated body 12 to a target treatment site within vasculature of a patient. For example, selective expansion of a subset of the plurality of balloons 30 (e.g., just one balloon or more than one but less than all the balloons 30) may help modify the position of elongated body 12 in a vessel relative to a center of the vessel, e.g., to re-center elongated body 12 in the vessel or to better position elongated body 12 for navigation around a curvature in the vasculature. As an example, a clinician may inflate only one or more balloons 30A-30C (shown in FIG. 2) along longitudinal half 17A of elongated body 12 to aid navigation. As balloons 30A-30C are inflated, balloons 30A-30F may apply a force directed radially outwards, pushing elongated body 12 away from vessel wall 58.

In other examples, at least two balloons 30 are fluidically coupled to the same inflation lumen. For example, elongated body 12 may define only one inflation lumen that is fluidically coupled to all the balloons 30 and used to deliver inflation fluid 50 to all the balloons. As another example, elongated body 12 may define multiple inflation lumens, but at least one of the inflation lumens is fluidically coupled to at least two balloons. FIG. 6 is a cross-sectional view similar to that shown in FIG. 5, except that elongated body 12 defines an inflation lumen 56 in fluid communication with at least two balloons 30A and 30D. Inflation lumen 56 can include, for example, an annular-ring shaped inflation lumen that is defined by the space between an inner and an outer wall of elongated body 12.

Depending on the relative cross-sectional diameter of carotid artery 47, balloons 30 may only be partially inflated with fluid 50 before balloons 30 engages with wall 58 of carotid artery 47. Balloons 30 may be inflated via fluid 50 to any suitable pressure. In some examples, balloons 30 may be inflated to a pressure of about 1-6 atmospheres via fluid 50 or at a specific pressure, such as 2-5 pounds per square inch (psi). In addition, balloons 30 may be configured to be deflated via a vacuum or other stable source applied to inflation lumens 54A, 54B, 56 to forcibly remove fluid 50 from balloons 30 (e.g., remove fluid at about 1 mL/min-10 ml/min).

In the inflated state within carotid artery 47, balloons 30 may conform to engage with the wall of carotid artery 47 to anchor elongated body 12 in carotid artery 47.

Balloons 30 may be of any suitable size or shape. In some examples, plurality of balloons 30 may define a cross sectional diameter in the inflated state equal to or greater than the cross-sectional diameter of carotid artery 47 (e.g., on the order of about 2 mm to about 4 mm). Additionally, or alternatively, balloons 30 may exhibit a cross sectional diameter that is configured to conform to a range of vessel diameters when inflated to the expanded state.

Figure 7:
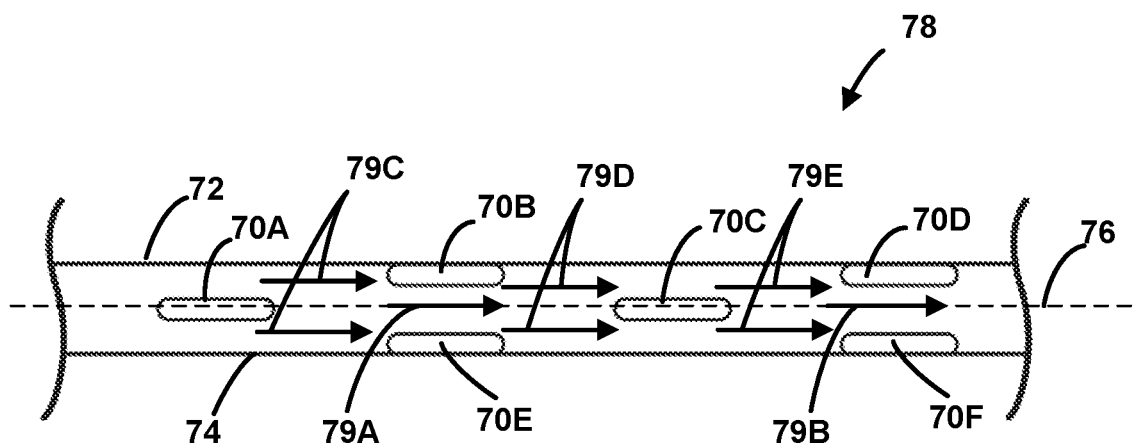
FIG. 7 is a side elevation view of another example catheter and illustrates another example staggered balloon arrangement.

As discussed above, in other examples, a plurality of balloons 30 that are circumferentially and longitudinally staggered can have different arrangements than that shown in FIGS. 2 and 3. FIG. 7 is a side elevation view of another example elongated body 72 of a catheter 78, which illustrates an example balloon arrangement showing a plurality of balloons 70A-70F (collectively "balloons 70") symmetrically distributed about a central longitudinal axis 76 of elongated body 72. Elongated body 72, balloons 70, and catheter 78 are similar to elongated body 12, balloons 30, and catheter 10 of FIGS. 1-3, except for the relative arrangement of balloons 70, and the description of elongated body 12 and balloons 30 is also applicable to elongated body 72 and balloons 70.

In the example shown in FIG. 7, the plurality of balloons 70 includes six balloons 70A-70F that are longitudinally and circumferentially staggered relative to each other along outer surface 74 of elongated body 72, but include some balloons that are circumferentially and/or longitudinally aligned. Balloons 70A, 70C are circumferentially aligned with each other, but circumferentially offset from balloons 70B, 70D, 70E, 70F; balloons 70B and 70D are circumferentially aligned with each other, but circumferentially offset from balloons 70A, 70C, 70E, 70F; and balloons 70E and 70F are circumferentially aligned with each other, but circumferentially offset from balloons 70A, 70B, 70C, and 70D. Balloons 70B, 70E are longitudinally aligned with each other, but longitudinally offset from balloons 70A, 70C, 70D, and 70F; and balloons 70D, 70F are longitudinally aligned with each other, but longitudinally offset from balloons 70A, 70B, 70C, and 70E.

In the circumferentially and longitudinally staggered balloon arrangement shown in FIG. 7, balloons 70B, 70E define a fluid passageway 79A through which fluid may flow past balloons 70B, 70E in a direction along longitudinal axis 76, and balloons 70D, 70F define a fluid passageway 79B through which fluid may flow past balloons 70D, 70F in a direction along longitudinal axis 76. Longitudinally adjacent balloons also define fluid passageways. For example, balloons 70A, 70B, 70E also define a fluid passageway 79C through which fluid may flow in a direction along longitudinal axis 76, balloons 70B, 70E, 70C define a fluid passageway 79D through which fluid may flow in a direction along longitudinal axis 76, and balloons 70C, 70D, 70F define a fluid passageway 79E through which fluid may flow in a direction along longitudinal axis 76.

In other examples, however, catheter 78 can include any suitable number of balloons such as one balloon, two, three, four, five, or more than six balloons in different arrangements that include at least some balloons (or balloon portions in the case of a single balloon) that are both circumferentially and longitudinally separated from another balloon (or balloon portion) to define a fluid passageway between the balloons (or balloon portions).

Figure 8:
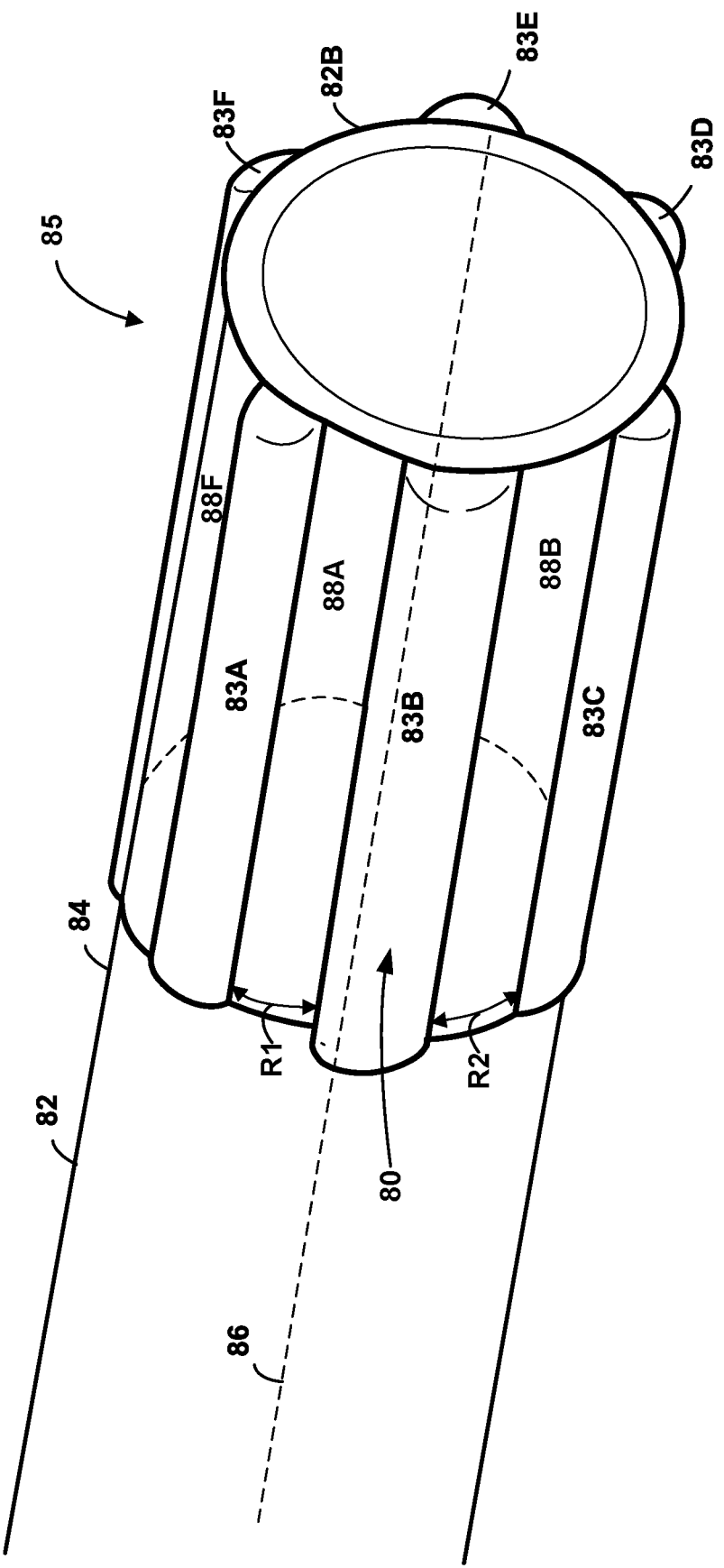
FIG. 8 is an example conceptual side view of another example portion of the catheter in FIG. 1 and illustrates another example configuration of a balloon.

FIG. 8 is another example conceptual side view of a portion of another example catheter 85, which includes an elongated body 82 and a single balloon 80 defining a plurality of lobes 83A-83F (collectively "lobes 83"). In other examples, lobes 83A-83F may be defined by separate balloons, e.g., as described with respect to balloons 30 of FIGS. 1-6, and the balloons may be arranged as shown with respect to the lobes 83 in FIG. 8. Catheter 85 and elongated body 82 are similar to catheter 10 and elongated body 12 of FIGS. 1-6, except for the balloon 80, and the description of catheter 10 and elongated body 12 is also applicable to catheter 85 and elongated body 82. In addition, balloon 80 may be similar to a balloon of plurality of balloons 30 of FIGS. 1-6. The portion of elongated body 82 shown in FIG. 8 can be a distal portion in some examples, where the distal portion includes distal end 82B of elongated body 82. As another example, the portion shown in FIG. 8 can be a more medial portion or a more proximal portion of elongated body 82. Balloon 80 may be positioned any suitable distance from distal end 82B of elongated body 82.

Balloon lobes 83A-83F shown in FIG. 8 are circumferentially staggered relative to each other, but at least partially longitudinally aligned, such that balloon lobes 83A-83F are at least partially coextensive in a direction along longitudinal axis 86. For example, the proximal ends of balloon lobes 83A-83F can be aligned with each other along longitudinal axis 86, and the distal ends of balloon lobes distal 83A-83F can be aligned with each other along longitudinal axis 86 in examples in which balloon lobes 83A-83F have the same length and are fully coextensive (and fully longitudinally aligned) in a direction along longitudinal axis 86. As another examples, at least two balloon lobe may have different lengths, such that the proximal and/or distal ends of these at least two balloons are not aligned, but the at least two balloon lobes are arranged to be at least partially coextensive in a direction along longitudinal axis 86.

In the example shown in FIG. 8, balloon 80 is welded at locations 88A-88F around outer surface 84 of elongated body 82. Welded locations 88A-88F define locations at which balloon 80 does not expand away from outer surface 84 of elongated body 82 or expand away from outer surface 84 less than an outermost surface of lobes 83, e.g., the surface furthest from an outer surface of elongated body 82 in a direction orthogonal to longitudinal axis 86.

In the example shown in FIG. 8, welded locations 88A-88F are spaced (e.g., evenly spaced or unevenly spaced) about an outer perimeter of elongated body 82 and aligned along central longitudinal axis 86. Welded locations 88A-88F are longitudinally aligned with each other and each welded location of locations 88A-88F is offset from an adjacent welded location in a circumferential direction. For example, welded location 88A is offset from an adjacent welded location 88B in a circumferential direction. In other examples, however, balloon 80 can be welded to elongated body 82 any suitable number of locations such as one location, two, three, four, five, or more than six locations. In addition, although weld locations 88A-88F are shown as only extending longitudinally to define lobes 83 that are circumferentially spaced from each other, in some examples, balloon 80 may be welded to elongated body 12 via a weld that defines lobes that are longitudinally spaced from each other, e.g., as shown with respect to balloons 30A, 30B, and 30C in FIG. 2.

An end view of elongated body 82 may look similar to the end view of elongated body 12 shown in FIG. 3.

Welded locations 88A-88F each define a location of a fluid passageway through which fluid may pass from a proximal side of balloon 80 to a distal side of balloon 80, or vice versa, in a direction along longitudinal axis 86. The fluid passageways may be defined by the surfaces of balloon 80 defining lobes 83, as well as the surfaces of balloon 30 welded to elongated body 12. If balloon lobes 83 are separate balloons, then the fluid passageways may be defined by the outer surfaces of the balloons and the outer surface of elongated body 82.

As discussed above, in some examples, a catheter comprising one or more balloons (e.g., balloons 30 or balloon 80) defining one or more fluid passageways can be used to deliver a therapeutic neurovascular device to a target treatment site within neurovasculature of a patient. For example, the catheter can be configured receive the therapeutic neurovascular device directly within a lumen of the catheter or receive the therapeutic neurovascular device via another catheter. Anchoring the catheter using the one or more balloons defining the one or more fluid passageways may facilitate a better therapeutic outcome by enabling the catheter to be anchored without blocking blood flow through neurovasculature or through blood vessels used to access the neurovasculature when delivering the therapeutic neurovascular device to the neurovasculature.

Figure 9:
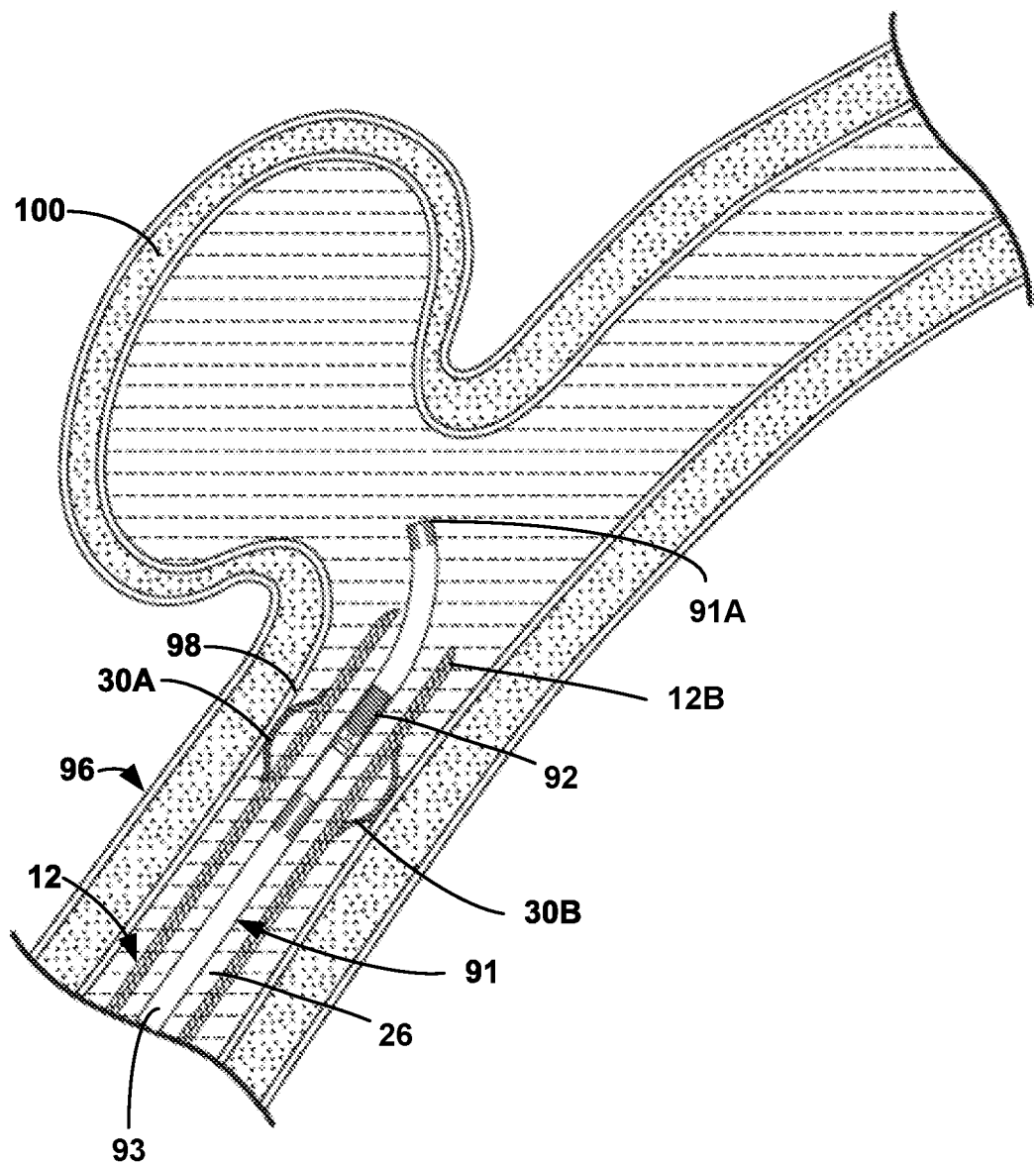
FIG. 9 is a cross-sectional view of the catheter of FIG. 1 in a blood vessel and illustrates a guidewire and an implantable medical device in a lumen of the catheter.

FIG. 9 is a cross-sectional view of elongated body 12 of FIG. 1 in a blood vessel 96 and illustrates an inner catheter 91 in inner lumen 26 of elongated body 12, where inner catheter 91 includes a therapeutic neurovascular device 92 in inner lumen 93 of inner catheter 91. Although FIG. 9 illustrates therapeutic neurovascular device 92 in inner catheter 91, in other examples, therapeutic neurovascular device 92 can be positioned directly in inner lumen 26 of elongated body 92 without inner catheter 91. In addition, although FIG. 9 is described with reference to elongated body 12 of FIG. 1, in other examples, a therapeutic neurovascular device 92 can be within a lumen of other elongated bodies described herein, including elongated body 72 of FIG. 7 and elongated body 82 of FIG. 8.

In the example shown in FIG. 9, therapeutic neurovascular device 92 is an implantable embolization device, such as an embolization coil. In other examples, however, elongated body 12 can include any suitable medical device configured to be used to treat a defect in neurovasculature of a patient or used to facilitate treatment of the neurovasculature. For example, the therapeutic neurovascular device can include a thrombectomy device, a flow diverter, a balloon catheter, a microvascular plug, an embolic retrieval device (e.g., a stent retriever or an aspiration catheter), or an implantable medical device, such as an embolic coil. As another example, the therapeutic neurovascular device can include a drug delivery catheter.

As illustrated in FIG. 9, implantable embolization device 92 has a primary shape that is configured to fit within inner lumen 26 of elongated body 12 (as well as in inner lumen 93 of inner catheter 91 in the example shown in FIG. 9).

A clinician may introduce elongated body 12 into blood vessel 96 of a patient over a guidewire (not shown in the figures) that is received within inner lumen 26, e.g., directly in inner lumen 26 or in inner lumen 93 of inner catheter 91. Once the distal end of elongated body 12 is at the desired position, the clinician may inflate balloons 30 or a subset of balloons 30 to anchor elongated body 12 inside blood vessel 96. As shown in FIG. 9 with respect to balloons 30A and 30B, when inflated, the balloons 30 may engage with inner wall 98 of blood vessel 96 to keep catheter 10 at the desired location (despite sharp bend(s) in elongated body 12 proximal of balloons 30 due to the challenging vascular anatomy) while still enabling blood to flow through vessel 96, which may help to free up the hands of the clinician during a medical procedure, e.g., to better control delivery of embolization device 92 at a particular location within blood vessel 96. In addition, because blood may continue to flow through vessel 96 even while catheter 10 is anchored within blood vessel 96, the clinician may take more time to select the implant location for embolization device 92 and/or to take other actions prior to or after implanting embolization device 92 in blood vessel 96 compared to examples in which blood flow through blood vessel 96 is blocked by an anchoring balloon or other anchoring mechanism.

Figure 10:
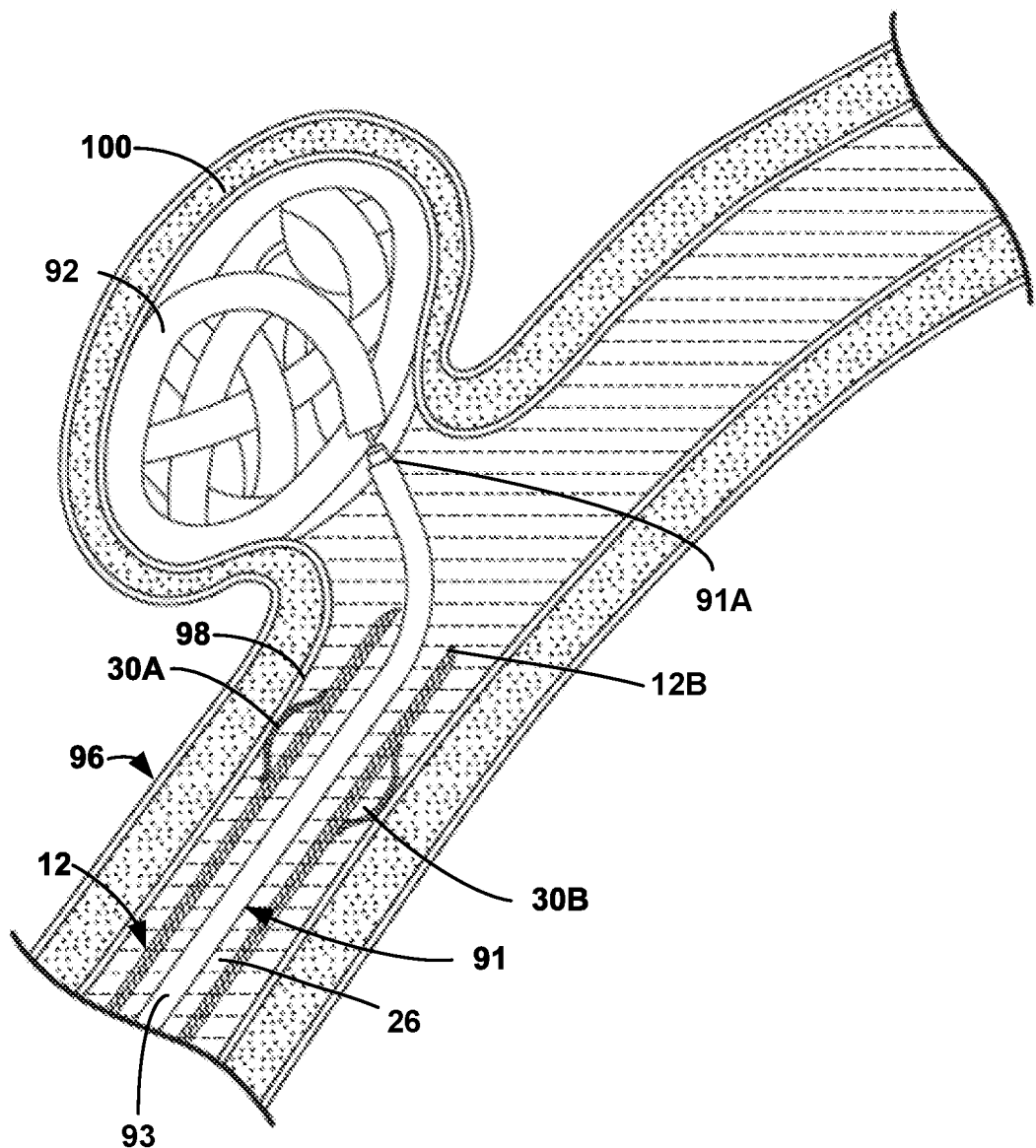
FIG. 10 is a cross-sectional view of the catheter of FIG. 1 in a blood vessel and illustrates an embolic coil being deployed from the lumen of the catheter.

After anchoring elongated body 12 within blood vessel 96, the clinician may advance and deploy implantable embolization device 92 through inner lumen 26 of elongated body 12 and into blood vessel 96. For example, in the example shown in FIGS. 9 and 10, a clinician may distally advance distal end 91A of inner catheter 91 past distal end 12B of elongated body 12 and proximate to or into aneurysm 100. Aneurysm 100 can be, for example, be in a brain of a patient. Although not shown in the figures, in some examples, elongated body 12 and/or inner catheter 91 can include radiopaque markers that enable a clinician to determine the relative position of elongated body 12 and/or inner catheter 91 relative to aneurysm 100 or another target site within a patient. The clinician may then deploy implantable embolization device 92 into aneurysm, as shown in FIG. 10. With the example implantable embolization device 92 shown in FIG. 9, once deployed at the desired location within blood vessel 96, implantable embolization device 92 takes on a secondary shape, as shown in FIG. 10. In its secondary shape, implantable embolization device 92 helps to minimize or event prevent blood flow into aneurysm 100.

Figure 11:
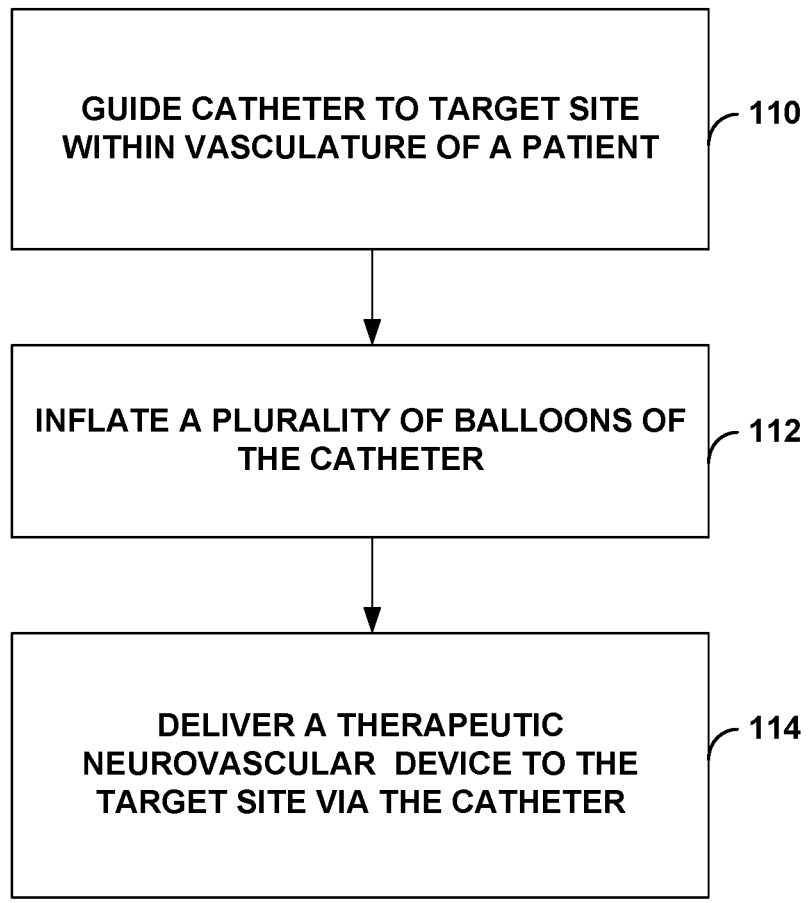
FIG. 11 is a flow diagram of an example method of delivering the catheter of FIG. 1 in a vascular of a patient.

FIG. 11 is a flow diagram of an example technique of using the catheters described herein. FIG. 11 is described below with reference to catheter 10 of FIGS. 1-3. However, in other examples, the example technique may be used with other catheters described herein.

In the technique shown in FIG. 11, a clinician navigates elongated body 12 of catheter 10 from a suitable access point (e.g., a femoral artery or a radial artery) to a target site within the vasculature of a patient (110). For example, the clinician can navigate elongated body 12 from a radial artery access point, through a common subclavian artery 46 (FIG. 4), and into a carotid artery 47 (FIG. 4) of a patient. In some examples, the clinician may deliver elongated body 12 to the target site with the aid of a guide member. For example, the clinician may introduce a guidewire introduced into the vasculature of a patient and elongated body 12 may then be advanced over the guidewire.

When distal end 12B of elongated body 12 is positioned as desired within the vasculature, the clinician can inflate the plurality of balloons 30 to an expanded state (112) to bring the balloons 30 into apposition with vessel wall 58 (FIG. 5) (112), which can help anchor elongated body 12 in the vessel and, on some cases, center elongated body 12 in the vessel. For example, the clinician can deliver inflation fluid 50 to plurality of balloons 30 via a plurality of inflation lumens 54 (FIG. 5) or via a single inflation lumen 56 (FIG. 6) to expand balloon 30 to an expanded state. As described above, when balloons 30 are in an expanded state, e.g., as shown in FIGS. 4-6, the balloons define one or more fluid passageways that enable to permit fluid to flow past the plurality of balloons 30 in a direction along central longitudinal axis 16, even while the balloons 30 are in apposition with vessel wall 58. Thus, catheter 10 is configured to anchor within a blood vessel without blocking blood flow through the blood vessel, e.g., and to the brain of the patient when delivering the therapeutic neurovascular device to the neurovasculature, which can provide better therapeutic outcomes or at least enable a longer medical procedure time compared to catheters that block blood flow through a blood vessel when anchored in the blood vessel.

In some examples of the technique of FIG. 11, the clinician delivers a therapeutic neurovascular device to a target treatment site within the patient via inner lumen 26 of elongated body (114).

Various examples have been described. These and other examples are within the scope of the following claims.

What is claimed is:

1. A catheter comprising: an elongated catheter body defining a lumen and defining a central longitudinal axis, the elongated catheter body having an outer surface extending both longitudinally along the central longitudinal axis and circumferentially about the central longitudinal axis; a plurality of balloons, wherein the plurality of balloons are longitudinally and circumferentially staggered along the outer surface of the elongated catheter body in a helical arrangement, the plurality of balloons including a first balloon, a second balloon, a third balloon, a fourth balloon, and a fifth balloon, the first, second, third, fourth, and fifth balloons having different circumferential positions along the outer surface of the elongated catheter body, wherein the second balloon is directly adjacent to the first and third balloons in at least a circumferential direction, the circumferential direction being orthogonal to the central longitudinal axis and extending about the central longitudinal axis with the central longitudinal axis being an axis of rotation of the circumferential direction, wherein when the first, second, third, fourth, and fifth balloons are fully expanded, there is: a first circumferential gap between the first and second balloons; a second circumferential gap between the second and third balloons; a third circumferential gap between the third and fourth balloons; and a fourth circumferential gap between the fourth and fifth balloons, such that an entirety of the first, second, third, fourth, and fifth balloons do not overlap in the circumferential direction, the first and second circumferential gaps extending less than fully around an outer perimeter of the elongated catheter body, wherein the first balloon, the second balloon, the third balloon, the fourth balloon, and the fifth balloon in the helical arrangement define a plurality of fluid passageways, wherein the fluid passageways of the plurality of fluid passageways are circumferentially offset from each other, wherein the each of the fluid passageways of the plurality of fluid passageways allows a fluid to flow outside of the lumen of the elongated catheter body and along the outer surface of the elongated catheter body in a longitudinal direction; and a therapeutic neurovascular device within the lumen of the elongated catheter body, wherein the therapeutic neurovascular device is configured to treat a defect in the vasculature of the patient while the plurality of balloons is expanded in the vasculature such that the plurality of balloons is in apposition with a vessel wall and fluid is flowing outside of the lumen of the elongated catheter body past and along an outer surface of a balloon of the plurality of balloons, and wherein the therapeutic neurovascular device comprises an embolic retrieval device, a thrombectomy device, a stent, a stent retriever, an embolic coil, a microvascular plug, a filter, a flow diverter, an aspiration catheter, a balloon catheter, or a drug delivery catheter.

2. The catheter of claim 1, wherein the plurality of balloons are configured to be inflated to an expanded state within vasculature of a patient to anchor the elongated catheter body within the vasculature, and wherein when the plurality of balloons are in an expanded state within the vasculature, the plurality of balloons is configured to permit blood to flow past the plurality of balloons in a direction along the central longitudinal axis.

3. The catheter of claim 1, wherein the plurality of balloons are symmetrically arranged about the central longitudinal axis.

4. The catheter of claim 1, wherein the plurality of balloons includes:
a first set of balloons on a first longitudinal half of the elongated catheter body; and
a second set of balloons on a second longitudinal half of the elongated catheter body, the first and second longitudinal halves being on opposite sides of the central longitudinal axis,
wherein for each of the first and second sets of balloons, each balloon of the respective set is offset from an adjacent balloon of the respective set in the longitudinal direction and the circumferential direction.

5. The catheter of claim 1, wherein each balloon of the plurality of balloons is longitudinally spaced from directly adjacent balloons in the longitudinal direction and the circumferential direction.

6. The catheter of claim 1, wherein each balloon of the plurality of balloons does not extend around an entire outer perimeter of the elongated catheter body.

7. The catheter of claim 1, wherein the elongated catheter body defines a plurality of inflation lumens, and wherein at least two balloons of the plurality of balloons are fluidically coupled to separate inflation lumens of the plurality of inflation lumens.

8. The catheter of claim 1, wherein balloons of the plurality of balloons are fluidically coupled to the lumen.

9. The catheter of claim 8, wherein the elongated catheter body defines a plurality of lumens including the lumen, wherein at least one other lumen of the plurality of lumens is fluidically isolated from the plurality of balloons.

10. A catheter comprising: an elongated body defining a lumen; at least five balloons along an outer surface of the elongated body, wherein the at least five balloons are configured to enable fluid to flow past and along an outer surface of the at least five balloons and through a blood vessel of a patient from a proximal side of the at least five balloons to a distal side of the at least five balloons when the at least five balloons are in an inflated state within the blood vessel and engaged with the blood vessel, wherein when the at least five balloons are fully expanded there is a circumferential gap between adjacent balloons of the at least five balloons such that an entirety of each balloon of the at least five balloons does not overlap in a circumferential direction with an adjacent balloon of the at least five balloons, wherein the at least five balloons define plurality of fluid passageways configured to allow fluid to flow outside of the lumen of the elongated body and along the outer surface of the elongated body in a longitudinal direction, wherein the fluid passageways of the plurality of fluid passageways are circumferentially offset from each other; and a therapeutic neurovascular device within the lumen of the elongated body, wherein the therapeutic neurovascular device is configured to treat a defect in vasculature of the patient while the one or more balloons are in the inflated state in the blood vessel such that the one or more balloons are in apposition with a vessel wall of the blood vessel and fluid is flowing outside of the lumen of the elongated body past and along the outer surface of the one or more balloons, and wherein the therapeutic neurovascular device comprises an embolic retrieval device, a thrombectomy device, a stent, a stent retriever, an embolic coil, a microvascular plug, a filter, a flow diverter, an aspiration catheter, a balloon catheter, or a drug delivery catheter.

11. The catheter of claim 10, wherein the one or more balloons are symmetrically distributed about a central longitudinal axis of the elongated body.

12. The catheter of claim 10, wherein the one or more balloons are asymmetrically distributed about a central longitudinal axis of the elongated body.

13. The catheter of claim 10, wherein the one or more balloons comprises a plurality of balloons longitudinally and circumferentially staggered along the outer surface of the elongated body.

14. The catheter of claim 10, wherein a balloon of the one or more balloons does not extend around an entire outer perimeter of the elongated body.

15. The catheter of claim 10, wherein the one or more balloons is only one balloon welded to the elongated body to define the one or more fluid passageways for the fluid to flow through the vasculature from a proximal side of the one balloon to a distal side of the one balloon.

16. A method comprising: introducing a catheter into vasculature of a patient, the catheter comprising: an elongated catheter body defining a lumen and defining a central longitudinal axis, the elongated catheter body having an outer surface extending both longitudinally along the central longitudinal axis and circumferentially about the central longitudinal axis; and a plurality of balloons, wherein the plurality of balloons are longitudinally and circumferentially staggered along the outer surface of the elongated catheter body in a helical arrangement, the plurality of balloons including a first balloon, a second balloon, a third balloon, a fourth balloon, and a fifth balloon, the first, second, third, fourth, and fifth balloons having different circumferential positions along the outer surface of the elongated catheter body, wherein the second balloon is directly adjacent to the first and third balloons in at least a circumferential direction, the circumferential direction being orthogonal to the central longitudinal axis and extending about the central longitudinal axis with the central longitudinal axis being an axis of rotation of the circumferential direction, wherein when the first, second, third, fourth, and fifth balloons are fully expanded, there is: a first circumferential gap between the first and second balloons; a second circumferential gap between the second and third balloons a third circumferential gap between the third and fourth balloons; and a fourth circumferential gap between the fourth and fifth balloons, such that an entirety of the first, second, third, fourth, and fifth balloons do not overlap in the circumferential direction, the first and second circumferential gaps extending less than fully around an outer perimeter of the elongated catheter body, wherein the first balloon, the second balloon, the third balloon, the fourth balloon, and the fifth balloon in the helical arrangement define a plurality of fluid passageways, wherein the fluid passageways of the plurality of fluid passageways are circumferentially offset from each other, wherein the each of the fluid passageways of the plurality of fluid passageways allows a fluid to flow outside of the lumen of the elongated catheter body and along the outer surface of the elongated catheter body in a longitudinal direction; anchoring the catheter by inflating the plurality of balloons; and delivering a therapeutic neurovascular device to a target site within the vasculature of the patient via the lumen of the catheter, wherein the therapeutic neurovascular device is configured to treat a defect in the vasculature of the patient while the plurality of balloons is expanded in the vasculature such that the plurality of balloons is in apposition with a vessel wall and fluid is flowing outside of the lumen of the elongated catheter body past and along an outer surface of a balloon of the plurality of balloons, and wherein the therapeutic neurovascular device comprises an embolic retrieval device, a thrombectomy device, a stent, a stent retriever, an embolic coil, a microvascular plug, a filter, a flow diverter, an aspiration catheter, a balloon catheter, or a drug delivery catheter.

17. The method of claim 16, wherein the plurality of balloons are configured to be inflated to an expanded state within the vasculature of the patient to anchor the elongated catheter body within the vasculature, and wherein when the balloons are in an expanded state within the vasculature, the plurality of balloons is configured to permit blood to flow past the plurality of balloons in a direction along the central longitudinal axis.

18. The method of claim 16, wherein the plurality of balloons are symmetrically arranged about the central longitudinal axis of the elongated catheter body.

* * * * *